United States Patent [19]
Schreiber et al.

[11] Patent Number: 6,080,910
[45] Date of Patent: Jun. 27, 2000

[54] TRANSGENIC KNOCKOUT ANIMALS LACKING IGG3

[75] Inventors: John R. Schreiber, Gates Mills; Neil S. Greenspan, Shaker Height, both of Ohio; Deborah S. Threadgill, Nashville, Tenn.; Terry Magnuson, Cleveland Heights, Ohio

[73] Assignee: Case Western Reserve University, Cleveland, Ohio

[21] Appl. No.: 08/803,120

[22] Filed: Feb. 20, 1997

[51] Int. Cl.⁷ .................................................. C12N 15/00
[52] U.S. Cl. .................................. 800/18; 800/13; 800/3; 800/21
[58] Field of Search .................................. 800/3, 13, 18, 800/21

[56] References Cited

U.S. PATENT DOCUMENTS

| | | | |
|---|---|---|---|
| 4,873,191 | 10/1989 | Wagner et al. | 800/25 |
| 4,873,313 | 10/1989 | Crawford et al. | 435/7.23 |
| 5,470,953 | 11/1995 | UGallatin et al. | 530/350 |
| 5,532,158 | 7/1996 | Suzuki et al. | 435/354 |
| 5,545,806 | 8/1996 | Lonberg et al. | 800/6 |

FOREIGN PATENT DOCUMENTS

| | | |
|---|---|---|
| WO 90/08832 | 8/1990 | WIPO . |
| WO 91/10741 | 7/1991 | WIPO . |
| WO 94/04467 | 3/1994 | WIPO . |
| WO 94/25585 | 11/1994 | WIPO . |

OTHER PUBLICATIONS

Campbell et al. (1997) Theriology, vol. 47 (1), 65–72.
Spriggs et al. (1992) Proc. Natl. Acad. Sci. USA, vol. 89, 607–6074.
Burstein et al. (1991) J. Immunol., vol. 147, 2950–2956.
Wigley et al. (1994) Reprod. Fertil. Dev., vol. 6, 585–588.
Shackelford et al. (1986) "Spectrum of IgG2 subclass deficiency in children with recurrent infections: Prospective Study," J. Pediat. 108:647–653.
Umetsu et al. (1985) "Recurrent Sinopulmonary Infection and Impaired Antibody Response to Bacterial Capsular Polysaccharide Antigen in Children with Selective IgG–Subclass Deficiency," N. Engl. J. Med. 313:1247–1251.
DeVelasco et al. (1995) "*Streptococcus pneumoniae*: Virulence Factors, Pathogenesis, and Vaccines," Microbiol. Rev. 59:591–603.
Wasserman (1990) "Antibody deficiency: IgG subclass deficiency and vaccine nonresponder states*," Pediatr. Infect. Dis. 9:424–433.
Thomas et al. (1993) "Colocalization of X–Linked Agammaglobulinemia and X–Linked Immunodeficiency Genes," Science 261:355–358.
Rawlings et al. (1993) "Mutation of Unique Region of Bruton's Tyrosine Kinase in Immunodeficient XID Mice," Science 261:358–361.
Scher (1982) "The CBA/N Mouse Strain: An Experimental Model Illustrating the Influence of the X–Chromosome on Immunity,"Adv. Immunol. 33:1–71.

Torres et al. (1996) "Aberrant B Cell Development and Immune Response in Mice with a Compromised BCR Complex," Science 272:1804–1808.
Shachar and Flavell (1996) "Requirement for Invariant Chain in B Cell Maturation and Function," Science 274:106–108.
Steeber et al. (1996) "Humoral Immune Responses in L–Selectin–Deficient Mice," J. Immunol. 157:4899–4907.
Köhler & Milstein (1976) "Derivation of specific antibody–producing tissue culture and tumor lines by cell fusion," Eur. J. Immunol. 6:511–519.
Goding (1986) "Production of Monoclonal Antibodies," in *Monoclonal Antibodies: Principles and Practice,* Academic Press, pp 59–103.
DePinho et al (1986) "Tailor–Made Monoclonal Antibodies," Annals of Internal Medicine 104:225–233.
Verheul et al. (1989) "Modulation of the Immune Response to Pneumococcal Type 14 Capsular Polysaccharide–Protein Conjugates by the Adjuvant Quil A Depends on the Properties of the Conjugates," Infect. & Immun. 57:1078–1083.
Pier (1982) "Safety and Immunogenicity of High Molecular Weight Polysaccharide Vaccine from Immunotype 1 *Pseudomonas aeruginosa,*" J. Clin. Invest. 69:303–308.
Pier et al. (1978) "Isolation and Characterization of a High–Molecular–Weight Polysaccharide from the Slime of *Pseudomonas aeruginosa,*" Infect. & Immun. 22:908–918.
Huang (1993) "Gene Targeting Technology for Creating Transgenic Models of Lymphopoiesis," Lab. Animal Sci. 43:156–159.
Evans et al. (1981) "Establishment in culture of pluripotential cells from mouse embryos," Nature 292:154–156.
Martin (1981) "Isolation of a pluripotent cell line from early mouse embryos cultured in medium conditioned by teratocarcinoma stem cells," Proc. Natl. Acad Sci. USA 78:7634–7638.
Magnuson et al. (1982) "The development of monosomy 19 mouse embryos," J. Embryo. Exp. Morph. 69:223–236.
Doetschman et al. (1988) "Establishment of Hamster Blastocyst–Derived Embryonic Stem (ES) Cells," Dev. Biol. 127:224–227.

(List continued on next page.)

*Primary Examiner*—Karen M. Hauda
*Assistant Examiner*—AnneMarie S. Beckerleg
*Attorney, Agent, or Firm*—Medlen & Carroll, LLP

[57] ABSTRACT

The present invention provides non-human transgenic animals in which an antibody subtype is selectively inactivated such that the transgenic animals express a reduced level of IgG3 relative to the levels expressed by the corresponding wild-type animal. Selective inactivation is achieved by the disruption through homologous recombination of the a nucleic acid sequence which encodes a constant region in the antibody subtype. The present invention provides transgenic animals which contain a disrupted Cγ3 gene. These transgenic animals retain the ability to express other antibody isotypes and subtypes. The present invention further provides methods for using these transgenic animals for screening candidate therapeutic compounds and for producing monoclonal antibodies which contain reduced levels of IgG3.

11 Claims, 14 Drawing Sheets

OTHER PUBLICATIONS

Tokunaga et al. (1989) "An Overcoming of "in Vitro 2–Cell Block" by Co–Culture with Embryonal Fibroblast Cells in the Mouse," Jpn. J. Anim. Reprod. 35:119–124.

Eistetter (1989) "Pluripotent Embryonal Stem Cell Lines Can Be Established from Disaggregated Mouse Morulae," Dev. Gro. Differ. 31:275–282.

Matsui et al. (1992) "Derivation of Pluripotential Embryonic Stem Cells from Murine Primordial Germ Cells in Culture," Cell 70:841–847.

Resnick et al. (1992) "Long–term proliferation of mouse primordial germ cells in culture," Nature 359:550–551.

Johnson et al. (1989) "Genetic Correction of Hereditary Disease," Fetal Ther. 4 (Suppl. 1):28–39.

Bradley et al. (1984) "Formation of germ–line chimaeras from embryo–derived teratocarcinoma cell lines," Nature 309:255–256.

Bradley et al. (1987) in *Teratocarcinomas and Embryonic Stem Cells: A Practical Approach,* Robertson E.J. (ed.), IRL Press, Oxford, U.K., pp. 113–151.

Nagy et al. (1990) "Embryonic Stem cells alone are able to support fetal development in the mouse," Development 110:815–821.

Jaenisch (1988) "Transgenic Animals," Science 240:1468–1474.

Brinster et al. (1985) "Factors affecting the efficiency of introducing foreign DNA into mice by microinjecting eggs," Proc. Natl. Acad. Sci. USA 82:4438–4442.

Cole–Strauss et al. (1996) "Correction of the Mutation Responsible for Sickle Cell Anemia by an RNA–DNA Oligonucleotide," Science 273:1386–1389.

Hammer et al. (1986) "Genetic Engineering of Mammalian Embryos," J. Animal Sci., 63:269–278.

Hammer et al. (1985) "Production of transgenic rabbits, sheep and pigs by microinjection," Nature 315:680–683.

Jaenisch (1976) "Germ line integration and Mendelian transmission of the exogenous Moloney leukemia virus," Proc. Natl. Acad. Sci. USA 73:1260–1264.

Jahner et al. (1985) "Insertion of the bacterial gpt gene into the germ line of mice by retroviral infection," Proc. Natl. Acad Sci. USA 82:6927–6931.

Van der Putten et al. (1985) "Efficient insertion of genes into the mouse germ line via retroviral vectors," Proc. Natl. Acad Sci. USA 82:6148–6152.

Stewart et al. (1987) "Expression of retroviral vectors in transgenic mice obtained by embryo infection," EMBO 6:383–388.

Jahner et al. (1982) "De novo methylation and expression of retroviral genomes during mouse embryogenesis," Nature 298:623–628.

Haskell & Bowen (1995) "Efficient Production of Transgenic Cattle by Retroviral Infection of Early Embryos," Mol. Reprod. Dev. 40:386–390.

Fedson & Musher (1994) "Pneumococcal Vaccine," In "Vaccines", Eds. Stanley Plotkin, and Edward Mortimer, Publ. W.B. Saunders Co. 517–564.

Alms & Bass (1967) "Immunization Against *Pseudomonas Aeruginosa*," J. Infect. Dis. 117:249–256.

Greenspan et al. (1987) "Interaction of IgG3 Anti–Streptococcal Group A Carbohydrate (GAC) Antibody With Streptococcal Group A Vaccine: Enhancing and Inhibiting Effects of Anti–Gac, Anti–Isotypic, and Anti–Idiotypic Antibodies," J. Immunol. 138:285–292.

Garcia–Gonzalez et al. (1988) "Purification of murine IgG3 and IgM monoclonal antibodies by euglobulin precipitation," J. Immunol. Meth. 111:17–23.

Jiskoot et al. (1991) "Purification and stabilisation of a poorly soluble mouse IgG3 monoclonal antibody," J. Immunol. Methd. 138:181–189.

Grey et al. (1971) "A New Mouse Immunoglobulin: IgG3," J. Exp. Med. 133:289–304.

Izui et al. (1993) "IgG3 cryoglobulins in autoimmune MRL–lpr/lpr mice: immunopathogenesis, therapeutic approaches and relevance to similar human diseases," Annals of the Rheumatic Diseases 52 (Suppl.) 1:S48–54.

Berney et al. (1992) "Selective pathogenicity of murine rheumatoid factors of the cryoprecipitable IgG3 subclass," Intern. Immunol. 4:93–99.

Greenspan & Cooper (1993) "Cooperative binding by mouse IgG3 antibodies: implications for functional affinity, effector function, and isotype restriction," Springer Semin. Immunopathol. 15:275–291.

Doetschman et al. (1985) "The in vitro development of blastocyst–derived embryonic stem cell lines: formation of visceral yolk sac, blood islands and myocardium.," J. Embryol. Expt. Morphol. 87:27–45.

Nagy et al. (1993) "Derivation of completely cell culture–derived mice from early–passage embryonic stem cells," Proc. Natl. Acad. Sci. USA 90:8424–8428.

Hooper (1989) "Using Embryonal Stem Cells to Introduce Mutations into the Mouse Germ Line," in *Vectors as Tools for the Study of Normal and Abnormal Growth and Differentiation,* Lother H. et al. (Eds.), Springer–Verlag, Berlin, NY, pp. 9–15.

Hooper et al. (1987) "HPRT–deficient (Lesch–Nyhan) mouse embryos derived from germline colonization by cultured cells," Nature 326:292–295.

Capecchi (1989) "Altering the Genome by Homologous Recombination," Science 244:1288–1292.

Pier (1985) "Pulmonary Disease Associated with *Pseudomonas aeruginosa* in Cystic Fibrosis: Current Status of the Host–Bacterium Interaction," J. Infect. Dis. 151:575–580.

Schreiber et al. (1991) "Anti–Idiotype–Induced, Lipopolysaccharide–Specific Antibody Response to *Pseudomonas aeruginosa.* II. Isotype and Functional Activity of the Anti–Idiotype–Induced Antibodies," J. Immunol. 146:188–193.

Schreiber et al (1990) "Anti–Idiotype–Induced, Lipopolysaccharide–Specific Antibody Response to *Pseudomonas aeruginosa,*" J. Immunol. 144:1023–1029.

Powderly et al. (1988) "T Cells Recognizing Polysaccharide–Specific B Cells Function As Contrasuppressor Cells In The Generation Of T Cell Immunity To *Pseudomonas aeruginosa,*" J. Immunol. 140:2746–2752.

Chen et al. (1993) "Immunoglobulin Gene Rearrangement In B Cell Deficient Mice Generated by Targeted Deletion Of The $J_H$ Locus," Int. Immunol. 5:647–656.

Chen et al. (1993) "B Cell Development In Mice That Lack One Or Both Immunoglobulin κ Light Chains," EMBO J. 12:821–830.

Cogné et al. (1994) "A Class Switch Control Region At The 3' End Of The Immunoglobulin Heavy Chain Locus," Cell 77:737–747.

Culliton (1997) "The microbial plague continues," Nature Med. (3)1:1.

Dietrich et al. (1994) "A genetic map of the mouse with 4,006 simple sequence length polymorphisms," Nat. Genetics 7:220–245.

Dietrich et al. (1996) "A comprehensive genetic map of the mouse gene," Nature 380:149–152.

Greenspan et al. Feb. 22–28, 1996 "Implications and Applications of Monogamous and Crosslinking Multivalent Antibody Binding," Keystone Symposium on Exploring and Exploiting Antibody and Ig Superfamily Combining Sites, Taos, New Mexico.

Harding & Lonberg (1995) "Class Switching in Human Immunoglobulin Transgenic Mice," Ann. NY Acad. Sci., 764:536–546.

Jakobovits et al. (1995) "Production of Antigen–Specific Human Antibodies from Mice Engineered with Human Heavy and Light Chain YACs$^a$," Ann. NY Acad. Sci., 764:525–535.

Kim et al. (1994) "Crossing the SJL λ locus into κ–knockout mice reveals a dysfunction of the λ 1–containing immunoglobulin receptor in B cell differentiation," EMBO 13:827–834.

Kitamura et al. (1991) "A B Cell–Deficient Mouse By Targeted Disruption Of The Membrane Exon Of The Immunoglobulin μ Chain Gene," *Nature* 350:423–426.

Koller et al. (1989) "Germ–line transmission of a planned alteration made in a hypoxanthine phosphoribosyltransferase gene by homologous recombination in embryonic stem cells," Proc. Natl. Acad. Sci. 86:8927–8931.

Kris et al. (1985) "Protection and Recovery in Influenza Virus–Infected Mice Immunosuppressed with Anti–IgM," J. of Immunol. (134)2:1230–1235.

Lamers et al. (1989) "Immune Status Of a μ, κ Transgenic Mouse Line. Deficient Response To Bacterially Related Antigens," Eur. J. Immunol. 19:459–468.

Lefranc et al. (1979) "Familial Lack of the IgG3 Subclass," J. Immunogen. 6:215–221.

Loefler (1996) "Microbes, chemotherapy, evolution, and folly," Lancet 348:1703–1704.

Loghem et al. (1980) "Gene Deletion and Gene Duplication Within the Cluster of Human Heavy–Chain Genes," J. Immunogen. 7:285–299.

McCormick et al. (1996) "Bispecific Antibodies Enhance In Vitro Killing of *Pseudomonas Aeruginosa* and *Staphylococcus Aureus* in the Context of Opsonin–Receptor Mismatch," FASEB J. 10(6)A1343:1983.

McCormick et al. (1994) "Bispecific Antibody Therapy for Cystic Fibrosis," Ped. Pulmonol. Suppl. 10:251–252.

McCormick et al. (1995) "Bispecific Antibodies Compensate for Elastase–Mediated Opsonin–Receptor Mismatch In Vitro," Ped. Pulmonol. Suppl. 12:245:235.

McCormick et al. (1996) "Bispecific Antibody (Anti–C3d/60.3) Compensates, In Vitro, for the Elastase–Mediated Opsonin–Receptor Mismatch of Cystic Fibrosis," Keystone Symposium: Exploring and Exploiting Antibody and Ig Superfamily Combining Sites, p. 45, abstract.

Miller et al. (1992) "A Single Autosomal Gene Defect Severely Limits IgG But Not IgM Responses In B Lymphocyte–Deficient A/WySnJ Mice," Eur. J. Immunol. 22:373–379.

Mond et al. (1989) "8–Mercaptoguanosine–Mediated Enhancement Of In Vivo IgG1, IgG2 and IgG3 Antibody Responses To Polysaccharide Antigens In Normal And xid Mice," Immunopharmacol. 18:205–212.

Press et al. (1982) "The H–2 Haplotype of a Thymus Graft Influences The Ir Gene Regulated IgG3, IgG1, IgG2b, and IgG2a Anti–(T,G)–A—L Antibody Responses of High–Responder $F_1$ Nude Mice," J. Immunol. 128:441–446.

Rosen (1989) "T Cell : B Cell Collaboration—The Response To Polysaccharide Antigens," Seminars in Immunol. 1:87–91.

Roth et al. (1995) "λ5, But Not μ, Is Required for B Cell Maturation in a Unique γ2b Transgenic Mouse Line," J. Exp. Med. 181:1059–1070.

Shahin et al. (1994) "Analysis of Protective and Nonprotective Monoclonal Antibodies Specific for *Bordetella pertussis* Lipooligosaccharide," Inf. and Immun. 62:722–725.

Tomasiewicz et al. (1993) "Genetic Deletion of a Neural Cell Adhesion Molecule Variant (N–CAM–180) Produces Distinct Defects in the Central Nervous System," Neuron 11:1163–1174.

Wels et al. (1984) "Structural analysis of the murine IgG3 constant region gene," EMBO 3:2041–2046.

Yoshida et al. (1996) "Defective B–1 Cell Development and Impaired Immunity against Angiostrongylus cantonensis in IL–5Rα–Deficient Mice," Immun. 4:483–494.

```
AAGTAGATAGGACAGATGGAGCAGTTACAGAGGAAAAGTTTGTAGAAGCTTGAATGTCCAGGCTGAGTATCTACATGGTGACTGGAAAAGGTGGCGTT         100
TGGGGAGGGGGACCAGATCAAGCTAAGGGTTCTGGGCAGATAGGAGTGTGGAAAAGTGACTGGTTATCACAAGGAACTAGGACAGAGGTGGTTGTGGG          200
GGAAGCCAGTGTGAGTGACCACAGTGTACTGAGGCAGGCTGTCTAGGGTCAGTGAAGCACAGAACTCAGTAGTTCTAGCCAGGCAACTAGG                300
AACACTCTGACAGGAAAGGTACATGAACCAGCCTGAGACCTTTGAAGACTCAGGCTCAGCCTGAGATGGCTCAGCAGTGGCAAGTGGGAATCCAGTGA         400
GGTGAGAGAACTGGAGACAGCTCCAGGGAAACTAGTCGTCTCCCTGCTCCCTGTAGCCACTCTGCACCTCATATCTGTACATGCCT                    500
ATTAGCAAGAAGATAGTAAGAGCTGGGTTCAGATATAAGACTGTGTGCAAGAACTAGATGGGTACTGGGTAGGAATGATGAAGAGAAAGGGAAAG          600
TGCTCAGGGCCTGTCTAACCCACAGCCAAGACAAGAATCAGTAAGAGAGAATCAGTAAGAGAGACAAGAAGCCTTGGCTGAGCAGGACAGGAAAGTCCCTGAGGCTAACAC  700
TCTCAAAAGGACCATATAGACAGTTCCTCAGTCGGGGGCCCATCTTGGTCCTGGAGATGAGGGAACTTACCATAGGAAGTCAAACTTGTTACAG             800
CCGTTATGTATACAGAGTTGGATGCACAGAGGAAGAAGGGCACATCAGGGTCTGAGCAGTGGAAGCCAGCTGTGTTCGAAGAAGGATGA                  900
CCCTGAAGCTGAGAGGAGACCTGGGTTGGAGAAAAAGACAGCCTGACACCTCTGTGACATAGGAAGGCAGGGTGAGTGTGGGTCAGGTAAGAGAAGAGGCA   1000
TAGAAAGAAATGGGAACTCATTGGAATCATTTGGTTTCCATTAGAAATACCCTGAACCTCAGGAGAAGTCAAGGAGGGCTGAGTCAAGCTGGAGC           1100
GTAGTGGAGCTAGAGCTGAGATGCCAGGAAGTTCATGACAGACTTACTGGGTGTGAACCTGAAGTGTCCCGTGGACACTGTCAGTGCAGAATCAGC           1200
GATGCCCATGCCAGGAGATTTAGGAATCAAAGTAGCAGCCAGGCAGGCTTAGCCTTGTCTATGATCAATGAGTTTGTGAAGAGCTCGTGGGCCTGAGACTAGGGCCGCCTA  1300
CCAGAGCCCAGATTTAGGAATCAAAGTAGCAGCCAGGCAGGCTTAGCCTTGTCTATGATCAATGAGTTTGTGAAGAGCTCGTGGGCCTGAGACTAGGGCCGCCTA        1400
CTGTAGCCAAGACCAACTCAGATGGCTTAGCCTGTAGAGAGAGAGAGAGAGAGAGACAGGAACAACATGCCAGGAGTCAGAGAAATGAAGCTCCATTGAGGGAAACATGAATGATGTC  1500
TTaattaaaAACAGGTCACAGAGAGAGGAATCAAAGGACAGGAGAGCTCCATTGAGGGAAACATGAATGATGTC                                1600
GAGAGAGAGAGAGGAATCAAAGGACAGGAGAGCTCCATTGAGGGAAACATGAATGATGTC                                              1700
TACAGCTTCAAGCACAGTGCAAGAGACTATAGAACAGTACATACAAACCAGCTTTCTGAAAATATGTTCAGGATAGAGCTGGGCTCAGAAATTCTACTG       1800
ATCAAACCTAGCTGCTAATTCTGGGTGGAGGGGTGTAAGGTGAGGCAATTGGAACCATCAAGGTTGCTATATGATGCCCTGACCTAGGTGATATATCC         1900
TACATGCTCTTTGCAGAACCCTGGCATCCTTGTAGGACCAAGGCTGAACTCCTCCAGGTGCCTGATCCAGCAGTCTGTCGATAACCTCACTCATCCTCCTAT   2000
```

FIG. 1A

```
CTTGCAGCTACAACAACAGCCCCATCTGTCTATCCCTTGTCCCTGGCTGCAGTGACCATCTGTGATCCTGGTGACACTGGGATGCCTTGTCAAAGGCT  2100
      CH1:  T  T  T  A  P  S  V  Y  P  L  V  P  G  C  S  D  T  S  G  S  S  V  T  L  G  C  L  V  K  G  Y
ACTTCCCTGAGCCGGTAACTGTAAAATGGAACTATGGAGCCCTGTCCAGCGGTGTGCGCACAGTCTCATCTGTCCTGCAGTCTGGGTTCTATTCCCTCAG  2200
  F  P  E  P  V  T  V  K  W  N  Y  G  A  L  S  S  G  V  R  T  V  S  S  V  L  Q  S  G  F  Y  S  L  S
CAGCTTGGTGACTGTACCCTCCAGCACCTGGCCCAGCCAGTGTCATCTGAACGTGTAGCCCATCCCGCCAGCAAGACTGAGTTGATCAAGAGAATCGT  2300
  S  L  V  T  V  P  S  S  T  W  P  S  Q  T  V  I  C  N  V  A  H  P  A  S  K  T  E  L  I  K  R  I  E
GAGAGGGTAACTAAGGAAataaaATTTAACCAGGAGTCAAGTTGGGGTCAACCTCTTATATAAAACAACCAAACTGAACAGACCTTGGCAGAGAGGCA  2400
ATGCCAATCAGGGCAGTTGGGTTCCTTGTCTACCTCCTAGAAGCCTCTTTTCATGTTCCTATATTCAGAAACACCTTGACTAGTGCTCTGGAATGTCACCAGT  2500
ATTTCACATCATGGACAAACAGAAGTAGACATGGGTCTCAACCTGTCAATGATCATATCCAGGAACACCTTGACCTAAGCCAACTAGGACCATCTTTC  2600
TTCTCCCTGGTTGCTCCCTCTGCCTTCCCTCTCCCTCTCTCCCTCTAAACCCCAGTCTTTTCTCTGCAGAGCCCAGTAATACCCAGTACCCCCCCCAGGTTC  2700
TTCATGCCCACGTAAGTCATTTAAGTCTCTAGTCCCAGAACATGATTGTCCCAAAGCCCACATGTTGGAGGATGGTACAGTTGCTAACCATCCTATCTC  2800
  S  C  P  P                HINGE:  P  R  I  P  K  P  S  T  P  P  G  S
TCCCCACCAGCTGGTAACATCTTGGGTGGACCATCCGTCTCTTCATCTTCCCCCCAAAGCCCAAGGATGCACTCATGATCTCCCTAACCCCCAAGTTACGT  2900
      CH2:   G  N  I  L  G  G  P  S  V  F  I  F  P  P  K  P  K  D  A  L  M  I  S  L  T  P  K  V  T  C
GTGTGGTGGTGGATGTGAGCGAGGAGGATGACCCAGATGTCCATGTGCAGCTGGTTGTGGACAACAAAGAAGTACACACAGCCTGGACACAGCCCCGTGAAGC  3000
  V  V  V  D  V  S  E  D  D  P  D  V  H  V  S  W  F  V  D  N  K  E  V  H  T  A  W  T  Q  P  R  E  A
TCAGTACAACAGTACCTTCCGAGTGGTCAGTGCCCCTCCCATCCAGCACTGGATGAGGGGCAAGGAGTTCAAATGCAAGGTCAACAACAAAGCC  3100
  Q  Y  N  S  T  F  R  V  V  S  A  L  P  I  Q  H  Q  D  W  M  R  G  K  E  F  K  C  K  V  N  N  K  A
CTCCCAGCCCCCATCGAGAGAACCATCTCAAAACCCAAAGGTGAGCTGCAGCTGACTGCAGCTGACTGCCTGACTGCATGGGGGCTGGATGGCATAAGaataaaGGTCTGTGT  3200
  L  P  A  P  I  E  R  T  I  S  K  P  K  G
```

FIG. 1B

```
GGACAGCCTTCTGCTTCAGCCACGAGACCTCTGTGTATGCTTCTAACCCCACAGAAGAGCCCCAGACACCTCAAGTATACACCATACCCCCACCTCGTGAAC      3300
                CH3: R  A  Q  T  P  Q  V  Y  T  I  P  P  P  R  E  Q
AAATGTCCAAGAAGAAGGTTAGTCTGACCTGCCTGGTCACCAACTTCTTCTCTGAAGCCATCAGTGTGGAGTGGGAAAGGAACGGAGAACTGGAGCAGGA          3400
 M  S  K  K  K  V  S  L  T  C  L  V  T  N  F  F  S  E  A  I  S  V  E  W  E  R  N  G  E  L  E  Q  D
TTACAGAACACTCCACCCATCCTGACTCAGATGGGACTTCCTCTACAGCAAGCTCACTGTGGATACAGACAGTTGGTTGCAAGGAGAAATTTTT            3500
 Y  K  N  T  P  P  I  L  D  S  D  G  T  Y  F  L  Y  S  K  L  T  V  D  T  D  S  W  L  Q  G  E  I  F
ACCTGCTCCGTGGTGCATGAGGCTCTCCATAACCACCACACAGAGAACCTGTCTCGCTCCCCTGGTAAATGAGAACAGCACTTAGCCATTCCTCGGG         3600
 T  C  S  V  V  H  E  A  L  H  N  H  H  T  Q  K  N  L  S  R  S  P  [G  K  .]
TCTTACAAGACACTGATACCAGCTCTAACTGTGAACCCTATAaataaaGCACCCAGAGATGGGACTTGTGAGATTATCTTGTTCTTTACATGGCACA         3700
TAGTTCATGATACACCCTCAGCCACCTCTGGGGTCTGTGGCAGGTGTCAAGGTGTAAGTTAACATCAAGAAAGAACAAGGTCTTATACTGCCAGACCC          3800
AGGGCATGCAAGTGGACCTGCCCCTTGCCCAGAGATCATCCCCTCTGCATAGCAAGTTGACCCAAGGGCCCCTTCATACTCTTCCCACAACCAGCAA          3900
CTGTTCTCTGTGAGTCTGGAGATAGTCATGGAAAATATCGCCCTAGAAGGAACACAGAAAGTGTATCCACCTCAACACGAACCCACCTTC            4000
ATTTGTCTGTCCTTCCCTGACTCCCTGACCTGTGTAAGTCTGGCCTAGGAGGTTCTCTGATGTATTACATAGACAGGAGAACTCATACATGAAGCCTG         4100
TTCATCTCCACCACCCCCAGCTGCCCCCAAGGAAGTAACATCAAATACCTCATGATGCTGAGACCAGAACTATTAGAACCAGCCTGCTAAGCATCACT         4200
AGAGACTTATGACCCTAGCTGCCCCCAAGGAAGTAACTACATATCAAATACCTCGATGATCGCAGCATGAATAGCTCCAAAACCCATCTTAGTGTCGGATATCCCTAG         4300
CAACCCACATGGTACCTCCAAGCTACCTACACATTGGACCAGTGAAGATGAAATAGCTCCTCATGGTACCTAACACTCTAACACACAAGTACTTCAGACCCAT          4400
ACACTACCTAAATGTACACATTGGACCCCTATTTCATCCTTACACTCTCGTGTACTCAGTTAACACTCCCTGTATAACATGACTCACTCCCAATGTGGACCTTCTAGGA          4500
TCTGTCCCTCTATGCCTAAGCCTTCTCAAGCCCCTTACACTCTCTCCCTGTCCCCTGTACTCAGTGACTCAGTGAGGGATAGGGAACAAGCAGTAGGTCAGGGTCAGAGCTATTA          4600
AGCCCAGTATCATCAAAAGCAGGCCCTCAATCAGCCAAGCCCAGACCCAGTAAGGTAGACAAAAGGGCTCCTCAGAGAACATAAAGGAGAGATGCCCCAGGAGG        4700
CCTACAGGGCTTCCAAGCCTTGAATCAGCCAAGCCCAGACCCAGTAAGGTAGACAAAAGGGCTCCTCAGAGAACATAAAGGAGAGATGCCCCAGGGAGG        4800
CCAGTGTATCTGGCTGTACCCAGGACAAAACGGCAGCACGTTGGGGAGCTGAGTTTCTGGTTCACAGAGAACATAAAGGAGAGATGCCCCAGGGAGG         4900
```

FIG. 1C

```
GTCTGCTGACCCAGTCAGGCTGCGAGCTTTCTCCTGGGCCCTCCTGCCACACAGGGAATGGCCCTAGCTCTCCTACCTTGTTGGGACAAAACACT      5000
GACTTTCCTCTCTGTTCAGAATGAGACCTGTGCTGAATGAGACCTGTGAGCCCAGATGGGAGCTGACGGCTCTGACGACCATCACCATCTTCATCA      5100
                     M1:  E   L   E   L   N   E   T   C   A   E   A   Q   D   G   E   L   D   G   L   W   T   T   I   T   I   F   I   S
GCCCTCCTCCTGAGCGTGTGCTACAGCGCCTCTGTCACCCTCTTCAAGGTCATCATCCCCTATTCCTCCACAATATCTACACTATACTCAAG         5200
L   F   L   L   S   V   C   Y   S   A   S   V   T   L   F   K
CTGTCTCCATAGTGATTCATGCTATCCCTACCTGTCTCCAATGTCTTTCCCATGTCATCATATGTCATCTTCCACATAGTCATCCACTGTA           5300
CTTACACCACCCTCTCCCTGTTCTATACTGTGCCCACATTGTCCCATGCTGTCTTGACACTCCCGCAAGTTGTCACCCACCC                    5400
TATCCATGCACCGTCTCCAATATGACTCTGCACACTGTCCTATTGCCGGTCCCCACTCGTTCCTCACCAAATCCCTACACTGTCCCTAC             5500
AATGCCCCCTGCTATAGCTACTACACCGTCTCAAAACTCTACTCACACCTGCTTATCCTCACTGTCTATCCTCTAGATATGACATCCAA             5600
GATTGGGAGCTGCCCCTGGCTTAGTGTATAATGAGGCAGGACTGACCTGTGAAGGGACTCAGGTCACACATAACATCCACTTTGCATCCACAGTG       5700
                                                                                           M2:  V
AAGTGGATCTTCTCCTCAGTGGTGCAGGTGAAGCAGGAACATGGACAAGGTGCCTAGCCTGTCTCTTCAGAAGGTG                          5800
K   W   I   F   S   S   V   V   Q   V   K   Q   T   A   I   P   D   Y   R   N   M   I   G   Q   G   A
CCAGAGCTTGCTAGCCCTCCAGTCCATGCAGTGAGCTGCTGAGCTGAGACACACAGGGTTACACTGCCTTCTCATCTCAGCATCCTTTGATCTTATGGC   5900
TCTGACTCTGCTACCCAGTCCCTTCACATTGGAGCAGCATGTGAAAGCAGGCTTGCCCCAGACCATAGCCAAGCAGACCACCACTACCAC            6000
AGCCAAAACAGTGGATAGGGTCCCCTGTGTGTTCTTCTTACAGTGTCTAGCCCTGTGTTCTAGCCCTGAAAAAACGTGCTTCTCTGAGAGAAGAAGTTTCC 6100
CATTTAGATGCAGATGAGCCTCAAAGGTCTCAAAGGAACTCTTTGGAAGGAACTGCCAAAGGTGACTCTAATGCCCTTCACCCAACCAGTGCCCTGCCC   6200
CTGAGAAGGCCTCAAAGGTGCACTGTACCTGTGAAGACCTCTTTCCTGCCATCATGGATGACTCAGAGGGCCTGAAGATCCAAGATGAAATCTCACTTCTTGG 6300
AATGTAAGATGGGGCTACTTGTACCTCAGTGGATGACTTACCTCAGTGGATGACTTCATAGCCTTCATGCTGCTGATCCCAC                    6400
AGCTTGAAGACCAGGGCACTGTTACCTGGCTTCAGTGGATGACTTACCTCAGTGGATGACTTCATAGCCTCTGTTGGGCCCTAGCACTGCTGATCCCAC  6500
GCCACTGAGCAAAGGCTGGGCAACCCAGAAAAGCCCGGTCAGTCCAAAGGTGGTCCAGGAGCAACATGGGTCCAGAGAGAG                      6600
```

FIG. 1D

```
AAAGGATGCTTAAAAAGCCAGGCAGGAATGGCCTTTCCTGCAGCCTGGCATCCGGACTGGGCCACTGACAGCAGAGAATACCAGTTAGAGTAGATATCC    6700
AGAGAGAGAGCCCAGGCCTGGGGCACTGAGGCTGACTGAGCTGCTGGCACTGTTGCTGTTTCTCCATTTCATATCAAGGCAAATGCAGGC            6800
CAGAGTCCCAGAAAAGACAAAGGAGAAATCCAGGAGAAGAAAGTTGGGTGCCCGGCTCTTAGGGACTCTAAGAGATGTTCACTGACTTGAAGCTTAGCT    6900
TTGCCAGCTTTTCTTTAAATTTCTGGAACCCAGCTATGTCTCTAAATGTCCCCTCCTTCATCTTTTTAATaataaaACATCCTTCAACATTGTAAAACAC  7000
ACTGTGTTCTTCCCTCTGTAGACCAACCCCCACTCTCCTTGTACAAAACTCACACACACATGCACACACACATGCACACTCACACAC               7100
ACGTACACTGCATGCAACAAGCACATTCACACACACATGCACACACACACTCACACATGCATGCACACAAATACATGCATCACACACCCACACC        7200
CACACATATACCAGCTCTAACATTCCCAAAGCACCCACTCACCCAGCATTCTGCTCTCAGTCTCAAGTCCCCTCCAACTATCATCCCATAATGAGGCAGGA 7300
TGGTCTGTGAGTGGGAATCACTGTGGATTCAGGCCATGGTGACCACGAGGAGAGGCAGTCAGGAAGCAGAGATAGCTAACATCCATGTGAGAGGAAC     7400
AGATGCTATGACTGACTCAAGAGTGGATTATAGCCTGATGACTTGCAGTAGGGCAGATAGCCCGGGAACGTGGCCTCCACTTGCACTGGTACAGGGCGAAAGC 7500
CTTTCTAAGGCAGATCAGGGGACTAGGGAAAGAAGATGAGCTCAGAGATGTCAGGGTGTGCTCTCGCTCTCCTTCCCAAGGTGAGTTTTGCAGCA       7600
GGAACATCCTACAACGGGTTCAACTGTTAGAAAACTGTTTGGGTCTACATAGGCCCTGGCAGAGAGATTGTGTTGGAGACTTGGGCTGGACTAGTCAAA    7700
AGACTCATGCAGCTG  7715
```

FIG. 1E

AAGCTTGAATGTCCAGGCTGAGTATCTACATGGTGACTGGAAAAAGGTGGGCGT
TTGGGGAGGGGACCAGATCAAGCTAAGGGTTCTGGGCAGATAGGAGTGTG
GAAAAGTGGACTGGGTTATCACAAGGGAACTAGGACAGGTGGTTGTGGGGA
AGCCAGTGTGAGTGACCACAGTGTACTGAGGCAGGCTGAGTGCTAGGGTAC
CAGGTCAAGCACAGGAACTCAGTAGGTCTAGCCAGGCAACTAGGAACACTCT
GACAGGAAAGGGTACATGAACCAGCCCTGAGACCTTTGAAGACCTGAGATGGCT
CAGGCAGCAGTGGCAAGTGAGGATGTGGGAATCCAGTGAGGTGAGAGAACTG
GAGACAGCTCCAGGAAAACTAGT

FIG. 3

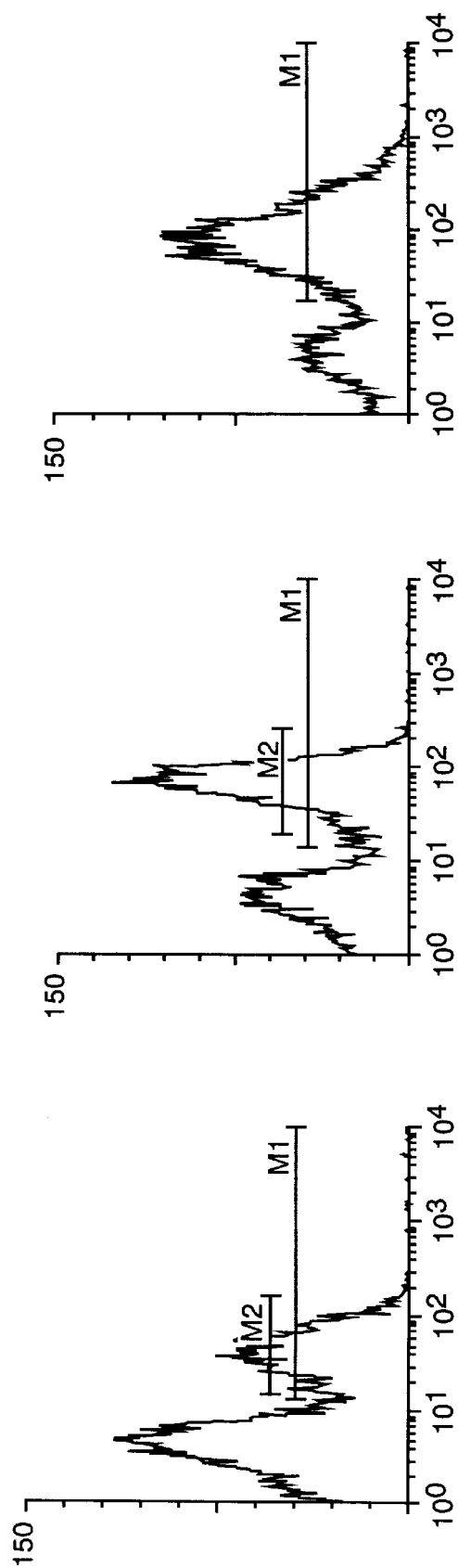

TRANSGENIC KNOCKOUT ANIMALS LACKING IGG3

This invention was made with government support under NAIAD-AI32596 awarded by NIH. The government has certain rights in the invention.

FIELD OF THE INVENTION

The present invention provides non-human transgenic animals in which an immunoglobulin subtype is selectively inactivated. In particular, the non-human transgenic animals provided by the present invention contain a disrupted γ3 gene which results in abrogation of expression of wild-type subclass IgG3. The present invention further provides methods for using these transgenic animals, and in particular for the screening of candidate therapeutic compounds.

BACKGROUND OF THE INVENTION

Disorders of the immune system are responsible for a multitude of human diseases which result in serious effects on the quality of life of individuals suffering from such disorders as well as of their family members. These disorders may stem either from an overproduction or underproduction of certain components of the immune system. Nowhere are the far reaching economic and health consequences of immune disorders better illustrated than in the recurrent infections in antibody-deficient individuals, and in the autoimmune disease systemic lupus erythematosus.

A) Recurrent Infection In Antibody-Deficient Individuals

Recurrent infection in individuals who are deficient in immunoglobulins with polysaccharide-coated bacterial pathogens (e.g., *Haemophilus influenzae, Streptococcus pneumoniae*, and group B streptococci) is a serious problem with significant clinical and economic consequences. For example, children with normal levels of immunoglobulins but subnormal levels of the IgG2 subclass have been found to have recurrent sinopulmonary infections as well as sepsis with polysaccharide encapsulated bacteria such as *H. influenzae* type b and pneumococcus (Shackelford et al. (1986) J. Pediat. 108:647; Umetsu et al. (1995) N. Engl. J. Med. 313:1247). In spite of the availability of antibiotics, the mortality of pneumococcal bacteremia in the last four decades has not dropped below 25%. [DeVelasco et al. (1995) Microbiol. Rev. 59:591–603]. In addition, because low serum IgG2 levels in adults are associated with failure to make an antibody response to polysaccharide vaccines (Umetsu et al. (1985) supra; Wasserman (1990) Pediatr. Infect. Dis. 9:424). IgG2-deficient adults are not protected against subsequent infection with polysaccharide-coated bacteria. This ineffective vaccination results in a serious waste of economic resources both at the level of the health worker whose efforts are better spent on individuals who are responsive to such immunization, as well as at the level of the IgG2-deficient individual whose subsequent infection results in repeated absence from work and a deterioration in the quality of life.

Available methods for the treatment of IgG2-deficiency in adults are limited to the administration of intravenous immunogobulin (IVIG). However, recent outbreaks of hepatitis in patients treated with IVIG has cast serious doubts on the usefulness of this approach. Furthermore, while the immunodeficient XID mouse may provide an animal model to evaluate immunization protocols against polysaccharide-coated pathogenic bacteria, the XID mouse is an unsuitable model. The XID mouse contains a missense mutation in the amino terminal of the Bruton's tyrosine kinase (btk) gene [Thomas et al., (1993) Science 261:355–358; Rawlings, et al., (1993) Science 261:358–361]. Although the XID mouse produces subnormal levels of antibodies in response to immunization with polysaccharides or hapten-polysaccharide conjugates, it is unclear whether this deficiency is the result of a deficiency in the production of IgM or some other immunoglobulin deficiency. This is due, in part to the expression of lowered serum levels of both IgM and IgG3 in the XID mouse [I. Scher, (1982) Adv. Immunol. 33:1]. Furthermore, while the levels of IgG3 in the XID mouse are reduced in relation to the wild type mouse from which they are derived, the XID mouse expresses significant levels of IgG3 both constitutively and following immunization with polysaccharide antigens [I. Scher, (1982) Adv. Immunol. 33:1; Thomas et al., (1993) Science 261:355–358]. While XID mice contain a single genetic defect, failure to attribute the pathological manifestations observed in these mice to a single underlying immunological defect precludes rational drug design.

B) Systemic Lupus Erythematosus (SLE)

Systemic lupus erythematosus (SLE) is a debilitating autoimmune disease with an annual incidence of about seven cases per 100,000. The clinical manifestations of SLE include fever, rash, arthritis, acute hemolytic anemia, thrombocytopenic purpura, pericarditis and a predisposition to bacterial infections. More importantly, patients with active SLE suffer from varying degrees of renal dysfunction, which range from proteinuria and pyuria to decreased glomerular filtration rate leading to nitrogen retention, electrolyte disturbance and acidosis. Renal disease is the most frequent source of morbidity and mortality in these patients.

While several mechanisms which result in autoimmune reactions have been proposed, the precise physiological mechanisms of SLE are not entirely understood. In particular, the determination of the biochemical and immunological mechanisms underlying renal disease is complicated by the multitude of pathophysiological symptoms associated with renal tissue damage. For example, renal disease may be attributed to any one or a combination of the associated elevation in circulating immune complexes, or to complement components and immunoglobulins which are found in diseased kidney tissue.

The treatment of SLE in general, and the associated renal dysfunction in particular, focuses on the alleviation of the general symptoms of the disease using one or a combination of two modalities, i.e., non-pharmacological treatment and pharmacological treatment. Non-pharmacological treatment includes periods of bed rest, avoiding exposure to sunlight, avoiding oral contraceptives and intrauterine devices, and long-term hemodialysis and kidney transplantation for the treatment of end-stage renal disease. Non-pharmacological treatment is often used as an adjunct to pharmacological treatment.

Pharmacological treatment includes the use of anti-inflammatory agents (e.g., salicylate), antimalarial drugs (e.g., chloroquine and hydroxychloroquine), corticosteroids, and cytotoxic drugs (e.g., cyclophosphamide). Unfortunately, most of the pharmacological approaches are controversial because few carefully controlled trials have been conducted. Moreover, many of the commonly used pharmacological agents have numerous side effects. For example, some patients with active SLE may experience aspirin-induced hepatitis. Antimalarial drugs may cause an irreversible retinopathy which leads to blindness, as well as skeletal muscle myopathy, cardiomyopathy and peripheral neuropathy. In addition, long-term corticosteroid use suffers from well known toxic effects. Attempts to reduce toxicity with alternate day dosage schedules are often unsatisfactory. Furthermore, the use of corticosteroids has not been proved to alter the ultimate course or outcome of glomerulonephritis in SLE. Treatment with pharmacological agents is further exacerbated by the nonresponsiveness by many patients with severe SLE who, paradoxically, are in most need of treatment.

To overcome ethical considerations (e.g., health safety, availability of willing subjects, etc.) which hamper the development of therapeutic agents for SLE-associated renal disease, animals have been proposed as a useful model for screening candidate therapeutic modalities. Several animals which bear gene alterations in humoral immune responsiveness are available [see e.g., Torres et al. (1996) Science 272:1804–1808; Leitges et al. (1996) Science 273:788–791; Shachar et al. (1996) Science 274:106–108; Steeber et al. (1996) J. Immunol. 157:4899–4907]. An example of such animals is the inbred MRL/MpJ-lpr/lpr mouse strain has been used as a model for SLE in humans. MRL/MpJ-lpr/lpr mice express unusual levels of cryoglobulins, primarily of the IgG3 subclass, elevated titers of immune complexes, and a diffuse glomerulonephritis. While the MRL/MpJ-lpr/lpr mouse exhibits some of the pathological abnormalities associated with renal disease in patients suffering from SLE, this animal is not suitable for the rational testing of drugs to alleviate or treat renal disease in SLE patients. This is due, in part, to the presence in the MRL/MpJ-lpr/lpr mouse of several genetic, immunologic and metabolic abnormalities. Because it would be unclear which, if any, of the genetic, immunologic and metabolic abnormalities exhibited by the MRL/MpJ-lpr/lpr mouse are affected by treatment for renal disease with a test drug, it is not feasible to rationally design drugs which target specifically those pathways which are modulated by that drug.

Thus, to date both non-pharmacological and pharmacological treatments provide unsatisfactory approaches to treating renal dysfunction associated with SLE because these approaches are generally ineffective, their effects are inconsistent, and are directed to alleviating the general symptoms of SLE, rather than specifically addressing the treatment of the most prevalent source of morbidity and mortality in SLE patients, i.e., renal disease. Moreover, no suitable animal models are currently available to rationally design drugs which target specific immunological mechanisms which cause nephritis in individuals suffering from SLE disease.

What is needed is a better model of these diseases. This model should be amenable to the testing of chemical compounds in the treatment of SLE-associated renal disease and of infection with bacterial pathogens.

SUMMARY OF THE INVENTION

The present invention provides transgenic non-human animals in which an antibody subtype is selectively inactivated. In particular, the present invention relates to selectively inactivating the IgG3 antibody subtype. The present invention further relates to the use of these transgenic animals for screening candidate therapeutic compounds.

In particular, the invention provides a transgenic non-human animal, wherein the animal expresses a reduced level of IgG3 relative to a corresponding wild-type animal.

While it is not intended that the mutation in the genome of the transgenic animals of the present invention be limited to a particular mutation, in one preferred embodiment the genome of the transgenic non-human animal comprises one or more deletions in one or more exons of a γ3 gene. In another preferred embodiment, the genome of the transgenic non-human animal comprising one or more deletions in one or more exons of a γ3 gene further comprises a frameshift mutation within the γ3 gene. In yet another preferred embodiment, the genome of the transgenic non-human animal comprising one or more deletions in one or more exons of a γ3 gene further comprises a heterologous selectable marker gene.

While it is not intended that the transgenic non-human animal of the invention be limited to a particular phenotype, in a preferred embodiment, the transgenic non-human animal of the invention is further characterized by being capable of expressing wild-type levels of an antibody selected from the group consisting of IgM and IgG2b.

While it is not intended to limit the invention to a particular type of non-human animal, in one preferred embodiment, the transgenic non-human animal of the present invention is a member of the order Rodentia. In a particularly preferred embodiment, the transgenic non-human animal of the present invention is a mouse.

The present invention also provides methods for screening a test compound for immunizing activity, wherein the methods comprises: providing (a) a first and second transgenic non-human animals, wherein the first and second transgenic non-human animals express a reduced level of IgG3 relative to a corresponding wild-type animal, and (b) a composition comprising the test compound; and administering the test compound to the first transgenic non-human animal to produce a treated animal.

In a preferred embodiment, the methods of the invention are contemplated to further comprise: administering live bacterium to (a) the treated animal, and (b) the second transgenic non-human animal to produce an infected animal; and measuring a reduction in infection of the treated animal relative to the infected animal and thereby identifying the compound as immunizing.

While not intending to limit the methods of the invention to any particular type of test compound, in one preferred embodiment, the test compound of the methods of the invention is a cell wall polysaccharide. In an alternative preferred embodiment, the test compound of the methods of the invention is a capsular polysaccharide.

Although it is not intended that the present methods be limited to a particular bacterium, in a preferred embodiment, the administered live bacterium is *Pseudomonas aeruginosa*. In an alternative preferred embodiment, the administered live bacterium is *Streptococcus pneumoniae*.

The invention also provides methods for identifying a compound as therapeutic for a disease, wherein the method comprises: providing (a) a transgenic non-human animal expressing a reduced level of IgG3 relative to a corresponding wild-type animal, (b) a non-human animal having the disease, and (c) a compound suspected of being capable of reducing IgG3 levels in an animal; mating the transgenic non-human animal with the diseased animal to produce an offspring animal having a reduced level of IgG3 relative to the diseased animal; detecting a reduction in disease symptoms in the offspring animal relative to the diseased animal, thereby identifying a reduction in IgG3 level as therapeutic; administering the compound to the diseased animal to produce a treated animal; and detecting a reduction in disease symptoms in the treated animal relative to the diseased animal, thereby identifying the compound as therapeutic.

While it is not intended that the methods of the invention be limited to a particular type of disease, in one preferred embodiment the diseased animal displays glomerulonephritis.

The invention further provides methods for producing a transgenic non-human animal, wherein the animal expresses a reduced level of IgG3 relative to a corresponding wild-type animal, and wherein the method comprises: providing (a) an embryonic stem cell comprising wild-type γ3 genes, (b) a blastocyst of a non-human animal, (c) a pseudopregnant non-human animal, and (d) an oligonucleotide sequence comprising at least a portion of a non-human γ3 gene, the portion comprising one or more deletions in one or more exons of the γ3 gene; introducing the oligonucleotide sequence into the embryonic stem cell under conditions such that the oligonucleotide sequence is homologously recombined into at least one of the wild-type γ3 genes in the genome of the embryonic stem cell to produce a treated embryonic stem cell; injecting the treated embryonic stem cell into the blastocyst to produce an injected blastocyst; introducing the injected blastocyst into the pseudopregnant non-human animal; and permitting the pseudopregnant animal to deliver progeny comprising the homologously recombined oligonucleotide, wherein the progeny express a reduced level of IgG3 relative to a corresponding wild-type animal.

While it is not intended that the methods of the invention be limited to a particular oligonucleotide sequence, in a preferred embodiment, the oligonucleotide sequence comprises a deletion of the nucleotide sequence of SEQ ID NO:9.

Although it is also not contemplated that the methods of the invention be limited to a particular phenotype of the progeny, in a preferred embodiment, the progeny are further characterized by expressing wild-type levels of an antibody selected from the group consisting of IgM and IgG2b.

While it is not intended to limit the methods of the invention to a particular type of non-human animal, in one preferred embodiment, the transgenic non-human animal is a member of the order Rodentia. In a particularly preferred embodiment, the transgenic non-human animal of the present invention is a mouse.

BRIEF DESCRIPTION OF THE DRAWINGS

FIG. 1 shows the nucleic acid sequence of the mouse γ3 gene (SEQ ID NO:1), and the amino acid sequence of CH1 (SEQ ID NO:2), H (SEQ ID NO:3), CH2 (SEQ ID NO:4), CH3 (SEQ ID NO:5), M1 (SEQ ID NO:6), M2 (SEQ ID NO:7).

FIG. 3 shows the nucleotide sequence of the 390 bp sequence (SEQ. ID NO.8) which was used as a probe to detect recombination of nucleotide sequences of the pγ3 targeting vector into genomic DNA.

FIG. 8 shows histograms of FACS analysis of B-lymphocytes treated with (a) anti-I-$A^d$ without mitogen, (b) anti-I-$A^d$ with mitogen, and (c) anti-mu (the M part of IgM heavy chain).

DEFINITIONS

Figure 2:
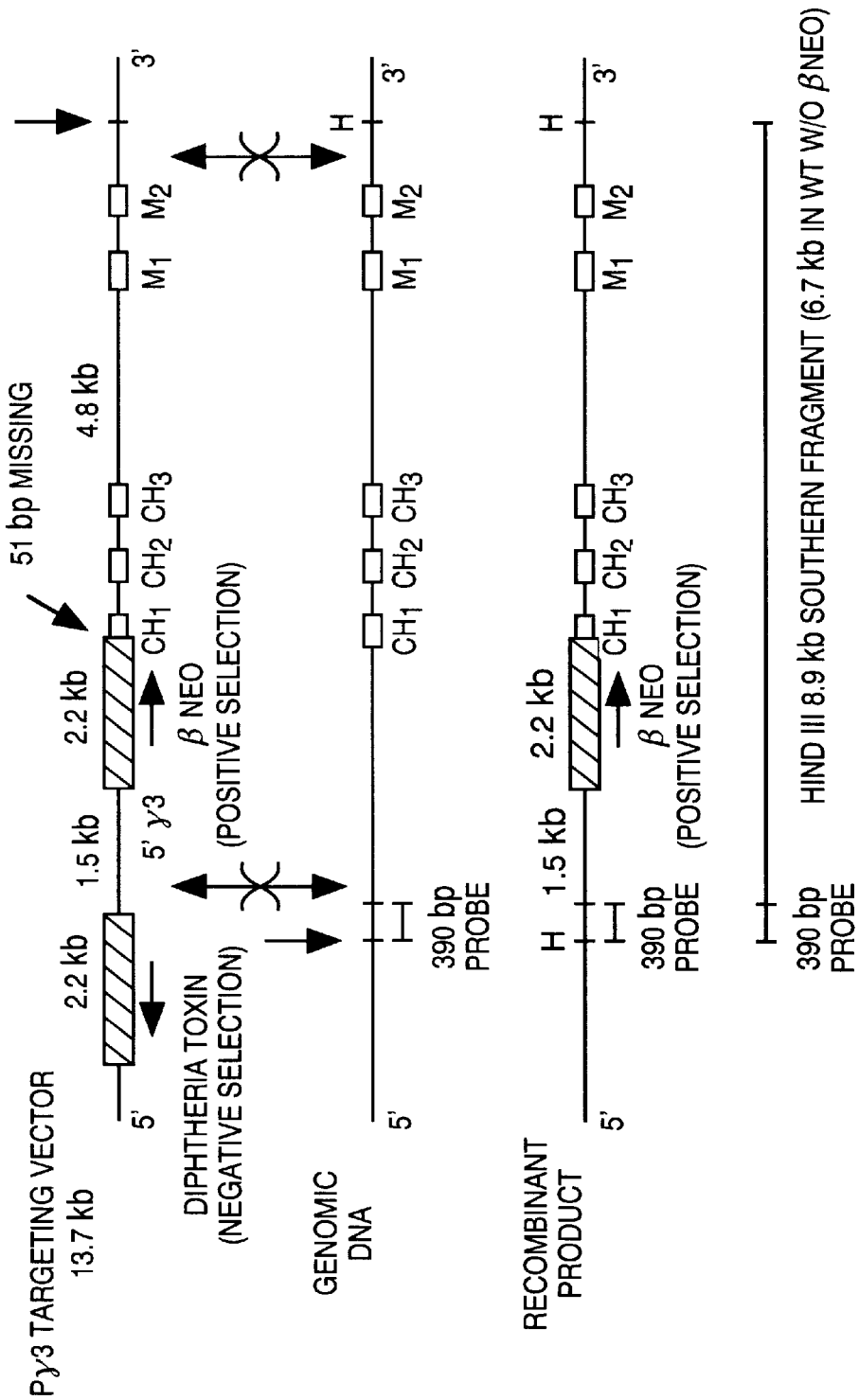
FIG. 2 shows the targeting strategy for disruption of the γ3 gene through homologous recombination.

To facilitate understanding of the invention, a number of terms are defined below.

The term "antibody" refers to a glycoprotein evoked in an animal by an immunogen (antigen). An antibody demonstrates specificity to the immunogen, or, more specifically, to one or more epitopes contained in the immunogen. Native antibody comprises at least two light polypeptide chains and at least two heavy polypeptide chains. Each of the heavy and light polypeptide chains contains at the amino terminal portion of the polypeptide chain a variable region, i.e., $V_H$ and $V_L$ respectively, which contains a binding domain that interacts with antigen. Each of the heavy and light polypeptide chains also comprises a constant region of the polypeptide chains (generally the carboxy terminal portion) which may mediate the binding of the immunoglobulin to host tissues or factors influencing various cells of the immune system, some phagocytic cells and the first component (C1q) of the classical complement system. The constant region of the light chains is referred to as the "$C_L$ region," and the constant region of the heavy chain is referred to as the "$C_H$ region." The constant region of the heavy chain comprises a $C_{H1}$ region, a $C_{H2}$ region, and a $C_{H3}$ region. A portion of heavy chain between the $C_{H1}$ and $C_{H2}$ regions is referred to as the hinge region, i.e. the "H region." The constant region of the heavy chain of the cell surface form of an antibody further comprises a spacer-transmembranal region (M1) and a cytoplasmic region (M2) of the membrane carboxy terminus. The secreted form of an antibody generally lacks the M1 and M2 regions.

As used herein, the term "heterologous antibody" is defined in relation to the transgenic non-human organism producing such an antibody. A heterologous antibody is an antibody having a modified amino acid sequence or a modified encoding DNA sequence as compared, respectively, to the wild-type amino acid sequence and the wild-type encoding DNA sequence in the transgenic non-human animal producing such an antibody.

The term "polyclonal antibody" refers to an antibody produced from more than a single clone of plasma cells; in contrast "monoclonal antibody" refers to an antibody produced from a single clone of plasma cells. Polyclonal antibodies may be obtained by immunizing a host organism with an immunogen and the resulting antibodies may be isolated from other proteins by using an affinity column, having an Fc binding moiety, such as protein A, or the like. Monoclonal antibodies can be obtained by various techniques familiar to those skilled in the art. Briefly, spleen cells from an animal immunized with a desired antigen are immortalized, commonly by fusion with a myeloma cell [see, Kohler and Milstein (1976) Eur. J. Immunol. 6:511–519; J. Goding (1986) In "Monoclonal Antibodies: Principles and Practice," Academic Press, pp 59–103]. Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host. Various techniques useful in these arts are discussed, for example, in Harlow and Lane, (1988) "Antibodies: A Laboratory Manual," Cold Spring Harbor, N.Y., including: immunization of animals to produce immunoglobulins; production of monoclonal antibodies; labeling immunoglobulins for use as probes; immunoaffinity purification; and immunoassays.

The term "isotype" or "class" when made in reference to an antibody refers to an antibody class that is encoded by a particular type of heavy chain constant region gene. Thus, different antibody isotypes differ in the amino acid sequence of the heavy chain constant ($C_H$) region. Several antibody isotypes are known, including IgA, IgD, IgG, IgE, and IgM. Thus, IgG possesses γ heavy chain constant domain (Cγ); IgM possesses μ heavy chain constant domain (Cμ); IgA possesses a heavy chain constant domain (Cα); IgD possesses δ heavy chain constant domain (Cδ); and IgE posseses ε heavy chain constant domain (Cε). Different antibody classes exhibit different effector functions and display different tissue localization. Each antibody class can be expressed as a membrane (m) or a secreted (s) form which differ in sequence at the carboxyl terminus of the heavy chain (reviewed by Blattner and Tucker (1984) Nature 307:417–422). Most antigens elicit prompt serum expression of IgM, followed later by a secondary isotype switching response in which products of downstream heavy chain genes, such as Cγ1 and Cγ2a predominate. The antibody isotype which predominates generally depends on the type of antigen (e.g., polypeptide, polysaccharide, etc.) used to elicit production of the antibody.

The terms "subtype" and "subclass" when made in reference to an antibody isotype, interchangeably refer to antibodies within an isotype which contain variation in the heavy chain structure. For example, the human IgG isotype contains the four subtypes IgG1, IgG2, IgG3, and IgG4, while the mouse IgG isotype contains the four subtypes IgG1, IgG2a, IgG2b, IgG3. Human IgA isotype contains IgA1 and IgA2 subtypes. The genes coding for the constant heavy chain have been mapped in mouse and are located on chromosome 12 in the order (from the 5' end) Cμ-Cδ-Cγ3-Cγ1-Cγ2b-Cγ2a-Cε-Cα corresponding to isotypes IgM, IgD, IgG3, IgG1, IgG2b, IgG2a, IgE and IgA.

The term "isotype switching" refers to the phenomenon by which one antibody isotype (e.g., IgM) changes to another antibody isotype (e.g., IgG). Similarly, the term "subtype switching" refers to the phenomenon by which an antibody subtype (e.g., IgG1) changes to another subtype (e.g., IgG2a) of the same antibody isotype.

The term "switch sequence" refers to a nucleic sequence responsible for switch recombination. Generally, a "switch sequence" is located upstream of a nucleic acid sequence which encodes the CH domain of an antibody [see, e.g., DePinho et al. (1986) Annals of Internal Medicine 104:225–233]. A "switch recombination" is the sequence of DNA recombination events which result in isotype switching or in subtype switching. Switch recombination generally refers to the recombination of two switch regions which results in the deletion of intervening nucleic acid sequences encoding immunoglobulin constant regions, thus placing a region coding for an immunoglobulin type or subtype in close proximity to the expressed variable-diversity-joining (VDJ) region genes, thereby resulting in antibody isotype switching or subtype switching. A "switch donor" sequence is a nucleic acid sequence, typically a μ switch sequence, and is 5' (i.e., upstream) of the nucleic acid sequence to be deleted during the switch recombination. A "switch acceptor" sequence is a nucleic acid sequence located between the DNA sequence to be deleted and the replacement constant region.

The "non-human animals" of the invention comprise any non-human animal whose genome contains an oligonucleotide sequence (e.g., a gene) encoding a modified form of IgG3. The modification renders the animal incapable of expressing IgG3 as detected, for example, by Western blot analysis and Enzyme-Linked Immunosorbent Assay (ELISA). Such non-human animals include vertebrates such as rodents, non-human primates, ovines, bovines, ruminants, lagomorphs, porcines, caprines, equines, canines, felines, aves, etc. Preferred non-human animals are selected from the order Rodentia which includes murines (e.g., rats and mice), most preferably mice.

The term "order Rodentia" refers to rodents i.e., placental mammals (class Euthria) which include the family Muridae (rats and mice).

The "non-human animals having a genetically engineered genotype" of the invention are preferably produced by experimental manipulation of the genome of the germline of the non-human animal. These genetically engineered non-human animals may be produced by several methods including the introduction of a "transgene" comprising nucleic acid (usually DNA) into an embryonal target cell or integration into a chromosome of the somatic and/or germ line cells of a non-human animal by way of human intervention, such as by the methods described herein. Non-human animals which contain a transgene are referred to as "transgenic non-human animals." A transgenic animal is an animal whose genome has been altered by the introduction of a transgene.

The term "transgene" as used herein refers to a foreign gene that is placed into an organism by introducing the foreign gene into embryonic stem (ES) cells, newly fertilized eggs or early embryos. The term "foreign gene" refers to any nucleic acid (e.g., gene sequence) which is introduced into the genome of an animal by experimental manipulations and may include gene sequences found in that animal so long as the introduced gene contains some modification (e.g., a point mutation, the presence of a selectable marker gene, etc.) relative to the naturally-occurring gene.

The term "gene" refers to a DNA sequence that comprises control and coding sequences necessary for the production of a polypeptide or precursor. The polypeptide can be encoded by a full length coding sequence or by any portion of the coding sequence so long as the desired activity of the polypeptide is retained.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and/or functional properties (i.e., altered characteristics) when compared to the wild-type gene or gene product. It is noted that naturally-occurring mutants can be isolated; these are typically identified by the fact that they have altered characteristics when compared to the wild-type gene or gene product.

The term "expresses a reduced level of IgG3 relative to a corresponding wild-type animal" as used herein in reference to a transgenic animal refers to a transgenic animal which contains a quantity of soluble or membrane-bound IgG3 antibody which is less than the quantity, respectively, of soluble or membrane-bound IgG3 in a corresponding wild-type animal, preferably 50% less than the quantity in a corresponding wild-type animal, more preferably 90% less than the quantity in a corresponding wild-type animals, and most preferably is at the background level of, or is undetectable by, an Enzyme Linked Immunosorbent Assay (ELISA) as described herein. When a background level or undetectable level of IgG3 is measured, this may indicate that IgG3 antibody is not expressed. A "reduced level of IgG3" need not, although it may, mean an absolute absence of expression of IgG3 antibody. The invention does not require, and is not limited to, a transgenic animal which does not express IgG3.

A "corresponding wild-type animal" refers to an animal which is isogeneic (i.e., has the same genetic background) and contains a wild-type γ3 gene.

The terms "wild-type γ3 gene" and "wild-type Cγ3 gene" are equivalent terms which refer to the nucleotide sequence (SEQ ID NO: 1) of the Cγ3 gene (FIG. 1) and allelic variants thereof. The term "wild-type IgG3" refers to an antibody containing heavy chain region which comprises the amino acid sequence of CH1 (SEQ ID NO:2), H (SEQ ID NO:3), CH2 (SEQ ID NO:4), CH3 (SEQ ID NO:5), M1 (SEQ ID NO:6), M2 (SEQ ID NO:7). Secreted wild-type IgG does not contain either M1 or M2. The art is well aware that certain modifications of SEQ ID NOS:1–7 can be made which will not interfere with the production of a polypeptide having an activity that is virtually indistinguishable from that of the wild-type IgG3; the present invention specifically contemplates these variant forms of IgG3. A "variant" of the mouse IgG3 is defined as an amino acid sequence which differs by one or more amino acids from the wild-type mouse IgG3 sequence. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software.

The terms "targeting vector" and "targeting construct" are used interchangeably to refer to oligonucleotide sequences comprising a γ3 gene. The terms "γ3 gene" and "Cγ3 gene" refer to a gene encoding the CH region of IgG3. It is preferred that the targeting vector also comprise a selectable marker gene. The targeting vector contains γ3 gene sequences sufficient to permit the homologous recombination of the targeting vector into at least one allele of the γ3 gene resident in the chromosomes of the target or recipient cell (e.g., ES) cells. Typically, though not necessarily, the targeting vector contains 2 kb to 10 kb of DNA homologous to the γ3 gene. This 2 kb to 10 kb of DNA may be located downstream or upstream of the selectable marker gene, or may be divided on each side of the selectable marker gene. In a preferred embodiment, the selectable marker gene is located upstream of the γ3 gene. The targeting vector may contain more than one selectable maker gene. When more than one selectable marker gene is employed, the targeting vector preferably contains a positive selectable marker (e.g., the neo gene) and a negative selectable marker [e.g., the Diphtheria toxin (dt gene) or Herpes simplex virus tk (HSV-tk) gene]. The presence of the positive selectable marker permits the selection of recipient cells containing an integrated copy of the targeting vector whether this integration occurred at the target site or at a random site. The presence of the negative selectable marker permits the identification of recipient cells containing the targeting vector at the targeted site (i.e., which has integrated by virtue of homologous recombination into the target site); cells which survive when grown in medium which selects against the expression of the negative selectable marker do not contain a copy of the negative selectable marker.

The targeting vectors of the present invention are of the "replacement-type;" integration of a replacement-type vector results in the insertion of a selectable marker into the target gene. As demonstrated herein, replacement-type targeting vectors may be employed to disrupt a gene resulting in the generation of a null allele (i.e., an allele incapable of expressing a functional protein; null alleles may be generated by deleting a portion of the coding region, deleting the entire gene, introducing an insertion and/or a frameshift mutation, etc.) or may be used to introduce a modification (e.g., one or more point mutations) into a gene.

The terms "selectable marker" or "selectable gene product" as used herein refer to the use of a gene which encodes an enzymatic activity that confers resistance to an antibiotic or drug upon the cell in which the selectable marker is expressed. Selectable markers may be "positive"; positive selectable markers typically are dominant selectable markers, i.e., genes which encode an enzymatic activity which can be detected in any mammalian cell or cell line (including ES cells). Examples of dominant selectable markers include, but are not limited to, (1) the bacterial aminoglycoside 3' phosphotransferase gene (also referred to as the neo gene) which confers resistance to the drug G418 in mammalian cells, (2) the bacterial hygromycin G phosphotransferase (hyg) gene which confers resistance to the antibiotic hygromycin and (3) the bacterial xanthine-guanine phosphoribosyl transferase gene (also referred to as the gpt gene) which confers the ability to grow in the presence of mycophenolic acid. Selectable markers may be "negative"; negative selectable markers encode an enzymatic activity whose expression is cytotoxic to the cell when grown in an appropriate selective medium. For example, the HSV-tk gene and the dt gene are commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme. Similarly, the expression of the dt gene selects against cells capable of expressing the Diphtheria toxin;

An animal whose genome "comprises a heterologous selectable marker gene" is an animal whose genome contains a selectable marker gene not naturally found in the animal's genome which is introduced by means of molecular biological methods. A heterologous selectable marker is distinguished from an endogenous gene naturally found in the animal's genome in that expression or activity of the heterologous selectable marker can be selected for or against.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "promoter element" or "promoter" as used herein refer to a DNA sequence that is located at the 5' end of (ie., precedes) a gene in a DNA polymer and provides a site for initiation of the transcription of the gene into mRNA.

The term "an oligonucleotide sequence comprising at least a portion of a non-human γ3 gene" refers to a polynucleotide sequence (i.e., a nucleic acid sequence) containing a nucleotide sequence derived from a non-human γ3 gene. This sequence may encode a portion of the IgG3 immunoglobulin (i.e., not the entire sequence); alternatively, this sequence may encode the entire sequence or may simply contain non-coding regions derived from the γ3 gene or a combination of coding and noncoding regions. The oligonucleotide may be RNA or DNA and may be of genomic or synthetic origin.

As used herein the term "portion" when in reference to a gene refers to fragments of that gene. The fragments may range in size from 10 nucleotides to the entire gene sequence minus one nucleotide. Thus, "an oligonucleotide comprising at least a portion of a gene" may comprise small fragments of the gene or nearly the entire gene.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

As used herein, the term "polymerase chain reaction" ("PCR") refers to the method of K. B. Mullis disclosed in U.S. Pat. Nos. 4,683,195, 4,683,202 and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

The term "surface polysaccharide" when made in reference to a bacterium refers to any polymer which comprises two or more monosaccharides, at least a portion of which is located on the bacterial surface, and is a T-independent type 2 antigen. By the term "bacterial surface" is meant a region outside the outermost bacterial cell membrane, including the peptidoglycan layer, cell wall and capsule. It is known in the art that gram-positive bacteria contain a single cell membrane, whereas gram-negative bacteria contain two cell membranes with a periplasmic space sandwiched between the two cell membranes. By the term "T-independent type 2 antigen" is meant a molecule which is capable of, among other things, inducing higher levels of soluble IgG3 in mouse or IgG2 in humans as compared to the levels of soluble mouse IgG3 or human IgG2 in the absence of treatment with the molecule. Serum levels of immunoglobulins may be determined using methods well known in the art which are exemplified by methods described herein. For example, serum immunoglobulin levels may be measured using Enzyme Linked Immunosorbent Assay (ELISA) and Western blots (see, e.g., Example 1). A surface polysaccharide may be a "cell wall polysaccharide" or a "capsular polysaccharide." Whereas capsular polysaccharides form a substantially continuous layer on the bacterial surface, cell wall polysaccharides form a discontinuous layer. A capsular polysaccharide generally contains repeating units of one or more oligosaccharide. An "oligosaccharide" as used herein refers to a polymer of two or more monosaccharides. A capsular polysaccharide may further contain additional components, e.g., acidic components (such as D-glucuronic acid or phosphate groups), ribitol, arabinitol, or phosphorylcholine. Capsular polysaccharides and their derivatives may be produced using methods well known to those of ordinary skill in the art [see, e.g., Verheul et al. (1989) Infect. & Immun. 57:1078–1083]. In contrast to a capsular polysaccharide, a cell wall polysaccharide generally, though not necessarily, does not contain repeating units of an oligosaccharide. An example of a cell wall polysaccharide is a *Pseudomonas aeruginosa* lipopolysaccharide O-specific side chain described by G. B. Pier (1982) J. Clin. Invest. 69:303–308 and Pier et al. (1978) Infect. Immun. 22:908–918.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening, e.g., using the screening methods of the present invention. A "known therapeutic compound" refers to a therapeutic compound that has been shown (e.g., through animal trials or prior experience with administration to humans) to be effective in such treatment or prevention.

A compound is said to be "in a form suitable for administration" when the compound may be administered to an animal by any desired route (e.g., oral, intravenous, subcutaneous, intramuscular, etc.) and the compound or its active metabolites appear in the desired cells, tissue or organ of the animal in an active form.

As used herein, the term "therapeutic amount" refers to that amount of a compound required to neutralize undesirable pathologic effects in a subject.

DESCRIPTION OF THE INVENTION

The present invention provides non-human transgenic animals in which an antibody subtype is selectively inactivated such that the transgenic animals express a reduced level of IgG3 relative to the levels expressed by the corresponding wild-type animal. Selective inactivation is achieved by the disruption through homologous recombination of a nucleic acid sequence which encodes a constant region in the antibody subtype. The present invention provides transgenic animals which contain a disrupted Cγ3 gene. These transgenic animals retain the ability to express other immunoglobulin isotypes and subtypes. The present invention further provides methods for using these transgenic animals for screening candidate therapeutic compounds directed against diverse diseases such as bacterial infection as well as nephritis associated with systemic lupus erythematosus (SLE). Additionally, the transgenic animals of the invention are useful for the generation of antibodies which contain substantially reduced levels of the IgG3 subtype.

The description of the invention is divided into the following sections: (A) generation of transgenic IgG3-KO animals, (B) screening compounds for antibacterial activity; (C) screening compounds for anti-glomerulonephritis activity, and (D) monoclonal antibody generation using the IgG3-KO animals.

A. Generation of Transgenic IgG3-KO Animals

The present invention provides trangenic non-human animals which express reduced levels of IgG3 relative to wild-type IgG3 levels. While it is not intended that the invention be limited by the particular nature of the knockout, the transgenic IgG3 knockout (IgG3-KO) animals provided herein contain a deletion in a $C_H$ region of the γ3 gene. More specifically, in a specific embodiment trangenic IgG3-KO mice animals were generated by introducing a neomycin cassette into a plasmid vector containing a 6.8 kb Hind III fragment of the γ3 locus such that 54 bp of the CH1 exon of the γ3 gene were deleted. For selection against nonhomologous recombination events, a diphtheria toxin gene was ligated at the 5' Spe I site of the γ3 gene. This construct was cloned into pBluescript SK+ (Stratagene) and linearized with Hind III (pγ3TV). The targeting vector was introduced into 129/Ola agouti strain embryonic stem cells (E14.1) via electroporation. Cells were plated and grown in a DMEM based selective medium containing G418.

Founder chimeric mice were then produced by injecting embryonic stem cells containing the targeted construct into blastocysts obtained post-fertilization of C57BL/6 female mice with C57BL/6 males. Injected blastocysts were transferred to the uterus of pseudopregnant F1 C3HBL/6 females. Resulting males (agouti/C57BL) expressing a chimeric coat color (>25% agouti/chinchilla agouti color) were bred to NIH Swiss Black mates. Germline chimeras produced progeny with an agouti coat color. Male and female agouti littermates (heterozygous agouti/C57BL/Swiss) were then crossed to obtain homozygous knockout pups.

The transgenic animals of the present invention are generated by introducing a targeting vector into a host cell. It is contemplated that the targeting vector contain a modified γ3 gene. The modification introduced into the γ3 gene may include, but is not limited to, an insertion, deletion, or substitution of one or more nucleotide sequences into one or more exons of the γ3 gene. It is further preferred that the modification be located in an exon encoding a constant region of the immunoglobulin. It is also further preferred that the constant region be a heavy chain constant region, e.g., CH1, CH2 and CH3. In a preferred embodiment, the modification is a deletion of 54 bp in the CH1 exon. In a preferred embodiment, the targeting vector does not contain sequences which modify the switch sequences for any of the genes which encode the constant domain of different class and subclass immunoglobulins. The retention of wild-type switch sequences is desirable in order to permit the transgenic animals of this invention to express immunoglobulin types (i.e., IgE and IgA) and subtypes (i.e., IgG1, IgG2b, and IgG2a) other than IgG3, whose constant regions (i.e., Cγ1, Cγ2b, Cγ2a, Cε, and Cα) are encoded by genes located downstream of the γ3 gene.

The transgenic IgG3-KO animals of the present invention may be produced by a variety of means. It is not required that the specific targeting vector employed herein be used. Where the transgenic animal is a mouse, any targeting vector containing a fragment of mouse γ3 genomic sequence which is capable of homologously recombining into the mouse γ3 gene in a manner that disrupts the γ3 gene (e.g., deletion, introduction of a frameshift, premature stop codon, missense mutation, etc.) may be employed. The targeting vector may be of the replacement- or insertion-type [Huang (1993) Lab. Animal Sci. 43:156]. Replacement-type vectors contain two regions of homology with the targeted gene flanking a selectable marker and result in the insertion of the selectable marker which thereby disrupts the targeted gene. In a preferred embodiment, the targeting vector is a replacement type vector wherein a neomycin positive selection gene is inserted into the CH1 exon of the γ3 gene and is flanked upstream and downstream by γ3 gene nucleotide sequences.

The targeting vector is not limited to replacement type vectors. Insertion-type vectors which contain a single region of homology with the targeted gene and result in the insertion of the entire targeting vector into the targeted gene are also contemplated to be within the scope of the invention.

Furthermore, the invention is not limited to the use of the neo gene as a positive selection marker. Other selection markers, including, but not limited to, the hyg gene and gpt gene, may also be used so long as the selection marker permits detection of the disruption of the wild-type γ3 gene with the vector sequence.

In one embodiment, the targeting vectors of the invention contain a negative selectable marker. In a preferred embodiment, the negative selectable marker is the dt gene. However, negative selectable markers are not limited to the dt gene, but are expressly contemplated to include other negative markers e.g., the HSV-tk gene.

It is not necessary that the targeting vector contain a selectable marker gene as discussed above, although the use of a selectable marker is preferred. Further, it is not necessary that, if a selectable marker is employed, the targeting vector employ both positive (e.g., neo) and a negative (e.g., dt) selectable marker gene.

The targeting vector may be introduced into a variety of host cells, e.g., oocytes, zygotes and embryonic stem (ES) cells. In a preferred embodiment, the host cell is an embryonal stem (ES) cell. Another method of introducing the vector into the animal's germ line involves using embryonic stem (ES) cells as recipients of the expression vector. ES cells are pluripotent cells directly derived from the inner cell mass of blastocysts (Evans et al., [1981] Nature 292:154–156; Martin [1981] Proc. Natl. Acad Sci. USA 78:7634–7638; Magnuson et al., [1982] J. Embryo. Exp. Morph. 81:211–217; Doetzchman et al., [1988] Dev. Biol., 127:224–227), from inner cell masses (Tokunaga et al., [1989] Jpn. J. Anim. Reprod., 35:113–178), from disaggregated morulae (Eistetter, [1989] Dev. Gro. Differ., 31:275–282) or from primordial germ cells (Matsui et al., [1992] Cell 70:841–847; and Resnick et al., [1992] Nature 359:550–551). Vectors can be introduced into ES cells using any method which is suitable for gene transfer into cells, e.g., by transfection, cell fusion, electroporation, microinjection, DNA viruses, and RNA viruses (Johnson et al., [1989] Fetal Ther., 4 (Suppl. 1):28–39). Once the expression vector has been introduced into an ES cell, the modified ES cell is then introduced back into the embryonic environment for expression and subsequent transmission to progeny animals. The most commonly used method is the injection of several ES cells into the blastocoel cavity of intact blastocysts (Bradley et al., [1984] Nature 309:225–256). Alternatively, a clump of ES cells may be sandwiched between two eight-cell embryos (Bradley et al., [1987] in *Teratocarcinomas and Embryonic Stem Cells: A Practical Approach*, Robertson E. J. (ed.), IRL Press, Oxford, U.K., pp. 113–151; and Nagy et al., [1990] Development 110:815–821). Both methods result in germ line transmission at high frequency.

Transgenes may also be introduced into ES cells by retrovirus-mediated transduction or by micro-injection. Transfected ES cells which contain the transgene may be subjected to various selection protocols to enrich for ES cells which have integrated the transgene assuming that the transgene provides a means for such selection. Alternatively, the polymerase chain reaction may be used to screen for ES cells which have integrated the transgene. This technique obviates the need for growth of the transfected ES cells under appropriate selective conditions prior to transfer into the blastocoel.

Transfected ES cells can thereafter colonize an embryo following their introduction into the blastocoel of a blastocyst-stage embryo and contribute to the germ line of the resulting chimeric animal. For review see Jaenisch, (1988) *Science* 240:1468–1474.

The generation of transgenic IgG3-KO mice need not employ ES cells. For example, embryonal cells at various developmental stages can be used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter which allows reproducible injection of 1–2 picoliters (pl) of DNA solution. The use of zygotes as a target for gene transfer has a major advantage in that in most cases the injected DNA will be incorporated into the host genome before the first cleavage [Brinster, et al. (1995) *Proc. Natl. Acad. Sci. USA* 82:4438–4442]. As a consequence, all cells of the transgenic non-human animal will carry the incorporated transgene. This will, in general, also be reflected in the efficient transmission of the transgene to offspring of the founder since 50% of the germ cells will harbor the transgene. Micro-injection of zygotes is the preferred method for incorporating transgenes in practicing the invention. U.S. Pat. No. 4,873191 describes a method for the micro-injection of zygotes; the disclosure of this patent is incorporated by reference herein in its entirety.

Alternatively, targeting vectors or transgenes may be microinjected into mouse oocytes to generate mice containing a disrupted γ3 gene. PCR can be employed to screen the targeted cells to identify cells containing a disrupted γ3 gene without the need to use a selectable marker and to subject the targeted cells to growth in selective medium. In addition, chimeric RNA-DNA oligonucleotides containing modified RNA residues (2'-O-methyl modification of the ribose) can be used to target mutations (e.g., the introduction of a frameshift, premature stop codon, etc.) into the γ3 gene using ES cells or oocytes to create trangenic IgG3-KO mice [Strauss et aL (1996) Science 273:1386].

Once the expression vector has been injected into the fertilized egg cell, the cell is implanted into the uterus of a pseudopregnant female and allowed to develop into an animal. Heterozygous and homozygous animals can then be produced by interbreeding founder transgenics. This method has been successful in producing transgenic mice, sheep, pigs, rabbits and cattle (See, Jaenisch [1988] supra; Hammer et al., [1986] J. Animal Sci., 63:269; Hammer et al., [1995] Nature 315:680–683; and Wagner et al., [1984] Theriogenology 21:29).

Retroviral infection can also be used to introduce transgenes into a non-human animal. The developing non-human embryo can be cultured in vitro to the blastocyst stage. During this time, the blastomeres can be targets for retroviral infection [Janenich (1976) *Proc. Natl. Acad. Sci. USA* 73:1260–1264]. Efficient infection of the blastomeres is obtained by enzymatic treatment to remove the zona pellucida [Hogan et al. (1986) in *Manipulating the Mouse Embryo*, Cold Spring Harbor Laboratory Press, Plainview, N.Y.]. The viral vector system used to introduce the transgene is typically a replication-defective retrovirus carrying the transgene [Jahner, D. et al. (1985) *Proc. Natl. Acad Sci. USA* 82:6927–6931; Van der Putten, et al. (1985) *Proc. Natl. Acad Sci. USA* 82:6148–6152]. Transfection is easily and efficiently obtained by culturing the blastomeres on a monolayer of virus-producing cells [Van der Putten, supra; Stewart, et al. (1987) *EMBO J* 6:383–388]. Alternatively, infection can be performed at a later stage. Virus or virus-producing cells can be injected into the blastocoele [Jahner, D. et al. (1982) *Nature* 298:623–628]. Most of the founders will be mosaic for the transgene since incorporation occurs only in a subset of cells which form the transgenic animal. Further, the founder may contain various retroviral insertions of the transgene at different positions in the genome which generally will segregate in the offspring. In addition, it is also possible to introduce transgenes into the germline, albeit with low efficiency, by intrauterine retroviral infection of the midgestation embryo [Jahner, D. et al. (1982) supra]. Additional means of using retroviruses or retroviral vectors to create transgenic animals known to the art involves the micro-injection of retroviral particles or mitomycin C-treated cells producing retrovirus into the perivitelline space of fertilized eggs or early embryos [PCT International Application WO 90/08832 (1990) and Haskell and Bowen (1995) Mol. Reprod. Dev. 40:386, hereby incorporated by reference].

The transgenic animals of the invention are not limited to animals which do not express IgG3 antibody. Rather, the invention includes a transgenic animal which contains a quantity of soluble or membrane-bound IgG3 antibody that is less than, preferably 50% less than, and more preferably 90% less than, the quantity of soluble or membrane-bound IgG3 antibody, respectively, in an isogeneic animal which contains a wild-type γ3 gene. Most preferably, the transgenic animals of the invention contain a quantity of IgG3 which is at the background level of, or is undetectable by, an Enzyme Linked Immunosorbent Assay (ELISA) as described herein.

The transgenic IgG3-KO animals provided by the present invention find several uses. For example, these animals may be used to screen the efficacy of candidate vaccines against bacterial infection, and in particular, infection with polysaccharide-coated bacteria. Additionally, these animals may be interbred with animals of a different genetic background which exhibit disease symptoms to generate transgenic knockout animals of a different genetic background. Such animals may be used to determine the involvement of IgG3 in disease development and to develop therapeutic compounds which target IgG3. Finally, such animals can be used to generate monoclonal antibodies where it is desirable that the monoclonal antibodies generated contain reduced levels of the IgG3 subclass as compared to IgG3 levels in monoclonal antibodies generated from animals containing a wild-type γ3 gene.

B. Screening Compounds for Antibacterial Activity

The transgenic IgG3-KO animals of the present invention provide a model for the determination of the efficacy of different vaccine candidates for the treatment of infection with polysaccharide-coated bacteria. Polysaccharide encapsulated bacteria pose a significant health risk. While antibodies to capsular polysaccharides have generally been shown to provide a protective immune response, polysaccharides are poor immunogens, particularly in young children below the age of 24 months, eliciting only low levels of clonally restricted antibodies [Fedson & Musher (1994) "Pneumococcal Vaccine," In "Vaccines", Eds. Stanley Plotkin, and Edward Mortimer, Publ. W.B. Saunders Co. 517–564]. Polysaccharides elicit typical T-independent type 2 responses in mammals. The antibodies generated are primarily of low titer and low intrinsic affinity. The early antibody response is characterized by production of large quantities of IgM, followed by IgG whose composition is highly dependent on antigen type and immunization regime. Furthermore, repeated immunization does not lead to a classical secondary response characterized by rapid production of high-titer, high-affinity antibodies as is seen with protein antigens. In mammals, the IgG antibody response to polysaccharides is restricted to a few subclasses, i.e., IgG3 in mice, and IgG1 and IgG2 in humans. Humans deficient in IgG2 have increased sinopulmonary infections with encapsulated bacteria. The mouse IgG3 is the immunobiological equivalent of human IgG2 and shares a similar ontogeny. Since both the ontogeny and immunobiology of mouse IgG3 and human IgG2 are similar, the transgenic IgG3-KO animals of the present invention are a useful model for human IgG2-deficiency i. Preparation of Antibacterial Compounds The animals of the present invention provide a useful model for screening candidate compounds for their ability to treat and protect individuals, in particular those individuals who are IgG2-deficient, against bacterial infection. The usefulness of the IgG3-KO transgenic mice of the present invention is based, in part, on the absence from these transgenic mice of the IgG3 subtype which, similarly to human IgG2, is the major immunoglobulin subtype induced in response to infection with polysaccharide coated bacteria. Polysaccharide coated bacteria include, but are not limited to bacteria which contain cell wall polysaccharides and capsular polysaccharides. Polysaccharide coated bacteria are known in the art and are exemplified by *Pseudomonas aeruginosa*. Bacteria containing capsular polysaccharides are exemplified by *Streptococcus pneumonia, Haemophilus influenzae*, and *Neisseria meningitidis*. In a preferred embodiment, the bacteria which contains capsular polysaccharides is *Streptococcus pneumoniae*.

Several types of compounds may be tested for their ability to immunize the transgenic mice of the present invention against infection with polysaccharide coated bacteria. Active immunization may be accomplished, for example, by using cell wall polysaccharides and/or capsular polysaccharides isolated from bacteria. Alternatively, passive immunization may be used by employing anti-polysaccharide antibodies. Antibodies may be murine or chimeric, i.e., contain sequences derived from more than one animal species. It is preferred that chimeric antibodies contain human amino acid sequences.

Cell wall polysaccharides are commercially available and may be produced using several methods known in the art [see, e.g., G. B. Pier (1982) J. Clin. Invest. 69:303–308; Pier et al. (1978) Infect. Immun. 22:908–918]. Generally, cell wall polysaccharides are isolated from crude slime which is obtained using routine methods e.g., the method of Alms and Bass [Alms & Bass (1967) J. Infect. Dis. 117:249–256]. Briefly, nucleic acids are removed from the crude slime by dissolving the slime in PBS, adding cetavalon (10% cetyl-trimethylammonium bromide) to 1% and allowing the mixture to stand at 22° C. for 30 min. The precipitated nucleic acids are removed by centrifugation, and the supernatant precipitated with alcohol to a final concentration of 80%. The precipitate is collected, redissolved in PBS and the cetavalon step repeated. Lipopolysaccharides are then removed by dissolving the alcohol precipitate in 1% acetic acid, pH 2.8 and heated at 90° C. for 18 hours. After cooling, the precipitated lipid of the contaminating lipopolysaccharide is removed by centrifugation. Lipids are then extracted from the acetic acid layer with chloroform and the polysaccharides precipitated from the aqueous layer by alcohol precipitation. Residual nucleic acids are removed by digestion with nucleases (ribonuclease and deoxyribonuclease). The remaining protein is removed by phenol extraction. The phenol and aqueous layers are separated by centrifugation, and the aqueous layer precipitated with alcohol to 80%. The precipitate is dissolved in PBS and gel purified e.g., on a G100 column.

Capsular polysaccharides may be used as candidate vaccines in the transgenic animals of the present invention. Capsular polysaccharides are available commercially and may be generated using methods well known in the art [see, e.g., Verheul et al. (1989), supra].

Alternatively, rather than active immunization using antigenic polysaccharides, the transgenic animals of the present invention may be used to test the efficacy of a passive immunization modality using antibodies raised against, for example, cell wall polysaccharides or capsular polysaccharides. Passive immunization relies on the use of an antibody which binds to an antigen in the bacterium of interest, wherein the antibody used to bind the antigen is not made in the animal which is used to test the efficacy of, or which is being treated with, the antibody. This is generally, accomplished by generating an immune response in a first animal. The serum of the first animal is then administered to the afflicted animal to supply a source of specific and reactive antibody. The administered antibody functions to some extent as though it were endogenous antibody, binding the antigen. The antibody may be polyclonal or monoclonal. It is preferred that the antibody be monoclonal. Methods for the generation of polyclonal and monoclonal antibodies are routine in the art [Harlow and Lane, (1988) supra]. The generation of monoclonal antibodies directed to cell wall polysaccharides is exemplified in Example 4, infra.

ii. Screening Candidate Antibacterial Vaccines

Candidate antibacterial vaccines are administered to homozygous (γ3 −/−) IgG3-KO transgenic animals of the present invention and to control wild-type (γ3 +/+) animals. It is preferred that the transgenic and wild-type animals have an isogenic background in order to minimize variation in the animals' response. The compounds being tested may be administered using any suitable route (e.g., oral, parenteral, rectal, controlled-release transdermal patches and implants, etc.). Generally speaking, the route of administration will depend on the stability of the compound, the susceptibility of the compound to "first pass" metabolism, the concentration needed to achieve a therapeutic effect, and the like. As is clearly demonstrated herein, the transgenic animals of the present invention, while producing substantially reduced levels of IgG3 relative to wild-type levels, are still capable of expressing other antibodies, e.g., IgM and IgG2b. Using this information, one of skill in the art may initially screen the ability of the candidate compound to induce the production of IgG subtypes other than IgG3, as well as isotypes other than IgG. A given compound's relative efficacy as an antibacterial vaccine in relation to other candidate compounds may be determined based on (1) the total level of immunoglobulins produced, (2) the level of one or more selected antibody isotype or subtype, or (3) functional assays, e.g., facilitation of phagocytosis and killing by neutrophils or monocytes. Methods for the determination of antibody isotypes and subtypes are provided herein in Example 1.

Following this initial screening, the efficacy of a compound in protecting against infection by a certain organism may further be tested by administering the compound either prior to, simultaneously with, or following challenge of test IgG3-KO animals of this invention with the organism of interest. Control IgG3-KO animals which are treated identically with the test IgG3-KO animals in all respects with the exception that they are not treated with the compound are also included. The end point measured depends on the organism used, and is generally directed to quantitating the severity of the symptoms of bacterial infection (e.g. by measuring animal mortality, number of organism cells colonizing target tissues, etc.) in test IgG3-KO animals and in control IgG3-KO animals. A compound which appears promising (e.g., which reduces or abrogates the symptoms of infection in a test IgG3-KO animal as compared with the symptoms in a control IgG3-KO animal) is further evaluated by administering various concentrations of the compound to transgenic IgG3-KO animals infected with the organism in order to determine an approximate therapeutic dosing range.

C. Screening Compounds For Anti-Glomerulonephritis Activity

Additionally, the IgG3-deficient transgenic mice of the present invention may be mated with mice of a different genetic background to generate IgG3-deficient transgenic mice of the same genetic background as that to which they are mated. For example, IgG3-deficient transgenic mice of the MRLIMpJ-lpr/lpr genetic background may be produced as described in Example 2, infra. These mice are useful to determine the efficacy of different modalities of treatment of glomerulonephritis which is associated with systemic lupus erythematosus.

A unique physiochemical property of murine IgG3 is its ability to self associate [DePinho et al. (1986) 104:225–233; Greenspan et al. (1987) J. Immunol. 138:285; Garcia-Gonzalez et al. (1988) 111:17–23; Jiskoot et al. (1991) J. Immunol. Methd. 138:181–189]. Self-association of IgG3 was recognized in the first description of mouse IgG3 (Grey et al. (1971) J. Exp. med. 133:289–304). Self-association of IgG3 through non-specific IgG3 Fc—Fc interaction and the generation of monoclonal cryoglobulins has been linked to the development of glomerulonephritis in the MRL/LpJ-lpr/lpr mice which spontaneously develop an autoimmune disease resembling systemic lupus erythematosus (SLE) [Izui et al. (1993) Annals of the Rheumatic Diseases 52 (Suppl.) 1:S48–54; Berney et al. (1992) Intern. Immunol. 4:93–99].

In a preferred embodiment, the transgenic animals of the present invention provide a method to screen therapeutic compounds for use in preventing or treating the symptoms of glomerulonephritis, which is associated with SLE in humans. This use employs breeding the transgenic mice of the invention with mice which exhibit glomerulonephritis. The usefulness of the transgenic animals provided in this invention derives, in part, from the fact that IgG3 in humans and in mice share the property of being the most self-aggregating immunoglobulin [Greenspan et al. (1993) Springer Semin. Immunopathol 15:275–291].

The transgenic mice of the present invention may be used to determine the efficacy of candidate therapeutic modalities in the treatment of nephritis associated with SLE. In an initial step, the role of elevated IgG3 levels in the development of glomerulonephritis is determined by comparing the pathological manifestations of glomerulonephritis (e.g., 'wire-loop' glomerular lesions) in homozygous γ3 −/− transgenic IgG3-KO mice relative to those in γ3 +/+ wild-type mice of the MRL/LpJ-lpr/lpr genetic background. An association between the absence of IgG3 levels and the reduction or absence of glomerulonephritis pathology in homozygous γ3 −/− transgenic mice suggests that a reduction in IgG3 levels is therapeutic.

Candidate therapeutic compounds may next be tested for their ability to reduce IgG3 levels in an animal. Examples of candidate therapeutic compounds include monoclonal anti-IgG3 antibodies, and antisense sequences directed to the γ3 gene. Candidate therapeutic compounds are administered to wild-type (γ3 +/+) and to control homozygous IgG3-KO (γ3 −/−) mice having a MRL/LpJ-lpr/lpr genetic background.

IgG3 antisense sequences are used to turn off genes encoding mouse IgG3 by transfecting a cell or tissue with expression vectors which express high levels of a desired mouse IgG3 antisense oligomer (e.g., 15–20 nucleotides) or larger fragment. Such constructs can flood cells with untranslatable antisense sequences which inhibit expression of the γ3 sequence either by inhibiting transcription of a mouse γ3 gene (by preventing promoter binding to the upstream non-translated sequence) or inhibiting translation of a mouse γ3 -encoding transcript (by preventing the ribosome from binding). Antisense sequences can be designed from various locations along the coding or control regions of the mouse γ3 gene shown in FIG. 1. Mice treated with vectors expressing γ3 antisense sequences are monitored for changes in the pathological symptoms associated with SLE. The alleviation or treatment of one or more of these symptoms in mice by an antisense sequence suggests that the antisense sequence may be useful in the treatment and/or prevention of SLE in humans.

D. Monoclonal Antibody Generation Using The IgG3-KO Animals

The IgG3-KO transgenic mice of the present invention may be used to generate monoclonal antibodies which contain reduced levels of the IgG3 subtype. Such monoclonal antibodies may be desirable for the reduction of the incidence of inflammation which is a consequence of self-aggregation of IgG3 in monoclonal antibody preparations. Additionally, the production of monoclonal antibodies which contain lowered levels of IgG3 may be desirable to increase the efficiency of purification of these antibodies in vitro since purification is hampered by insolubility of the immunoglobulin to be purified, and since IgG3 immunoglobulins are insoluble as a result of their self-aggregation at the high concentrations necessary for antibody purification. Furthermore, it may be desirable to produce monoclonal antibodies of a subtype other than IgG3 to exploit the different immunological properties of these subtypes. The ability of the transgenic animals of the invention to switch to antibody subtypes other than IgG3 makes them a useful tool for such a purpose.

The IgG3-KO transgenic mice provided herein may be used to produce monoclonal antibodies by various techniques familiar to those skilled in the art. Briefly, spleen cells from a IgG3-KO animal immunized with a desired antigen are immortalized, commonly by fusion with a myeloma cell [see, Kohler and Milstein (1976) Eur. J. Immunol. 6:511–519; J. Goding (1986) In "Monoclonal Antibodies: Principles and Practice," Academic Press, pp 59–103]. Immunization may be with antigen or with intact cells.

Immunization with antigen may be accomplished in the presence or absence of an adjuvant, e.g., Freund's adjuvant. One of skill in the art knows that the use of adjuvant may influence the class of antibody produced. Typically, 10 $\mu$g antigen in 50–200 $\mu$l adjuvant or aqueous solution is administered per mouse by subcutaneous, intraperitoneal or intramuscular routes. Booster immunization may be given at intervals, e.g., 2–8 weeks. The final boost is given approximately 2–4 days prior to fusion and is generally given in aqueous form rather than in adjuvant.

Immunization with intact cells generally involves intraperitoneal injection of a dose of from $2 \times 10^6$ to $5 \times 10^7$ cells. Recipient IgG3-KO transgenic mice may be boosted at intervals of 3–8 weeks, and fusion performed 2–4 days after the last boost.

Spleen cells from the immunized IgG3-KO mice may be prepared by teasing the spleen through a sterile sieve into culture medium at room temperature, or by gently releasing the spleen cells into medium by pressure between the frosted ends of two sterile glass microscope slides. The cells are harvested by centrifugation (400 x g for 5 min.), washed and counted.

Spleen cells are fused with myeloma cells to generate hybridoma cell lines. Several myeloma cell lines which have been selected for sensitivity to hypoxanthineaminopterin-thymidine (HAT) are commercially available and may be grown in, for example, Dulbecco's modified Eagle's medium (DMEM) (Gibco BRL) containing 10–15% fetal calf serum. One of skill in the art knows that because most currently available mouse myeloma cell lines used for hybridoma production are of BALB/c origin, the IgG3-KO trangenic mice used for immunization as well as the mice used as recipients of the resulting hybridomas are preferably of a BALB/c genetic background in order to avoid rejection by the recipient mouse of the hybridomas which display the histocompatibility antigens of the myeloma cells. IgG3-KO transgenic animals having a BALB/c genetic background may be produced as described herein. Fusion of myeloma cells and spleen cells may be accomplished using polyethylene glycol (PEG) or by electrofusion using protocols which are routine in the art. Fused cells are distributed into 96-well plates followed by selection of fused cells by culture for 1–2 weeks in 0.1 ml DMEM containing 10–15% fetal calf serum and HAT. The supernatants are screened for antibody production using methods well known in the art. Hybridoma clones from wells containing cells which produce antibody are obtained, e.g., by limiting dilution. Cloned hybridoma cells ($4-5 \times 10^6$) are implanted intraperitoneally in recipient mice, preferably of a BALB/c genetic background. Sera and ascites fluids are collected from mice after 10–14 days.

EXPERIMENTAL

The following examples serve to illustrate certain preferred embodiments and aspects of the present invention and are not to be construed as limiting the scope thereof.

In the experimental disclosure which follows, the following abbreviations apply: g (gram); L (liter); $\mu$g (microgram); ml (milliliter); bp (base pair); kb (kilobases); ° C. (degrees Centigrade); AP (alkaline phosphatase); BSA (bovine serum albumin); PBS (phosphate buffered saline); pNPP (p-Nitrophenyl Phosphate); Becton-Dickinson (San Jose, Calif.); Biorad (Richmond, Calif.); Cappel Antibodies (Westchester, Pa.); Charles River (Michigan, Ohio); Corning (Coming, N.Y.); Dynatech (Chantilly, Va.); Gibco BRL (Grand Island, N.Y.); Harlan Olac, Ltd. (Oxon, U.K.); Harlan Sprague Dawley (Indianapolis, Ind.); Invitrogen (San Diego, Calif.); Jackson Laboratories (Bar Harbor, Me.); Molecular Dynamics (Sunnyvale, Calif.); Operon (Alameda, Calif.); Pharmingen (San Diego, Calif.); Schleicher & Schuell (Keene, N.H.); Southern Biotechnology (Birmingham, Ala.); Sigma (St. Louis, Mo.); Stratagene (La Jolla, Calif.); Taconic (German Town, N.Y.)

EXAMPLE 1

Generation of Transgenic Mice Containing a Disrupted Murine γ3 Gene

The complete germline nucleotide sequence of the Cγ3 gene (SEQ ID NO:1) and the predicted amino acid sequences encoded by the CH1 (SEQ ID NO:2), H (SEQ ID NO:3), CH2 (SEQ ID NO:4), CH3 (SEQ ID NO:5), M1 (SEQ ID NO:6), and M2 (SEQ ID NO:7) codons of the Cγ3 gene have been previously reported [Wels et al. (1984) EMBO J. 3:2041–2046] and are shown in FIG. 1. In order to generate transgenic mice which contain a disrupted murine γ3 gene, two targeting vectors containing a deletion in the CH1 exon of a murine γ3 gene were constructed and homologously recombined into the genome of embryonic stem cells. The deleted 54 bp of CH1 was replaced by a neomycin cassette. The resulting targeted embryonic stem cells were injected into mouse blastocysts and allowed to develop into chimeric mice which transmitted the disrupted murine γ3 gene in their germline as demonstrated by PCR and southern blot analysis of tail DNA. These steps are described below.

A) Targeting Vector Construction

The strategy used to design the targeting vector (pγ3) for disruption of the γ3 gene is outlined in FIG. 2. Briefly, a 13.7 kb targeting vector which contains the mouse γ3 gene CH2, CH3, M1, M2 exons, a 54 bp deletion in the CH1 exon which is replaced by β-neo gene, and a dt gene is homologously recombined into the γ3 gene of mouse genomic DNA to generate a recombinant γ3 gene which contains a CH1 exon from which 54 bp has been deleted and replaced with a β-neo gene sequence.

Two targeting vectors were constructed using this strategy. The first vector contained a γ3 gene isolated from a BALB/c library [Liu et al (1980) Science 209:1348–1353; Adams et al. (1980) Nucleic Acids Res. 24:6019–6032; Wels et al., (1984) EMBO J. 3:2041–2046]. However, since this vector resulted in a low targeting efficiency when homologously recombined with agouti embryonic stem cells (discussed below), a second targeting vector containing isogeneic DNA was constructed. In this targeting vector the murine γ3 gene was cloned from an agouti 129 library (Stratagene) using a 390 bp probe (SEQ ID NO:8) (FIG. 3), and the cloned gene was mapped by restriction digestion. The neomycin resistance gene driven by the β-actin promoter [Tomasiewicz et al. (1993) Neuron 11:1163–1174] was cloned into the CH1 exon, flanked by 6.5 kb on the 5' side and 1.8 kb on the 3' side. The cloning of neo resulted in the deletion of 54 bp [ACAACAACAGCCCCATCTGTCTATCCCTTGGTCCC TGGCTGCAG TGACACATCT (SEQ ID NO:9)] of CH1 and permitted positive selection for neomycin resistance. The diphtheria toxin (dt) gene [Tomasiewicz et al. (1993) supra] was inserted at the 5' SpeI site of the γ3 gene in the linear targeting sequence. The dt gene was used as a negative selection strategy instead of the thymidine kinase gene since the dt gene results in the production of toxin which is lethal to the cell unless the gene is eliminated during homologous recombination (Threadgill et al. (1995) Science 269:230), and since it allows negative selection without using the expensive drug gancyclovir. The targeting vector which contained the disrupted γ3 gene was cloned into Bluescript (Stratagene, La Jolla, Calif.) and then transformed into DH5α E. coli (Gibco BRL).

B) Homologous Recombination and Screening of Embryonic Stem Cells

The targeting vector was linearized and introduced by electroporation into embryonic stem cells (described below). Electroporation using a Biorad Gene Pulser (Biorad, Richmond, Calif.) at 675 V/cm was carried out in DMEM with 15% fetal calf serum, 1000 U/ml leukemia inhibitory factor (LIF; ESGRO™, Gibco/BRL) to reduce differentiation, 2 mM L-glutamine and $5 \times 10^{-5}$ β-mercaptoethanol. Ten minutes after electroporation the cells were plated onto murine embryonic fibroblasts (MEF) for selection. After 24 hours, 250 μg/ml of G418 was added and selection continued for 10 days. Surviving colonies were then picked, trypsinized, and transferred to 96-well plates. After a further 48 hours, replicate plates were made from surviving colonies and one set was frozen at −80° C. in freezing medium containing 10% DMSO for subsequent expansion of targeted lines after screening. Embryonic stem cells in the other replicate plate were grown to confluence and then used for the preparation of genomic DNA for Southern Blot analysis according to the method of Ramirez-Solis et al. (1992) Analytic Biochem. 201:33. Clonal lines from the 96-well plate described above which contained an homologous recombination event were screened by Southern blotting with a junctional 390 bp (Hind III/SpeI) fragment (FIG. 3) from the murine γ3 locus which was not present in the targeting vector (FIG. 2).

Genomic DNA from transfected ES cells was digested overnight using HindIII, then loaded onto 1% agarose gels and electrophoresed for 375 Vh. Following denaturation for 2 h in 0.5N NaOH containing 1.5 M NaCl (with one change after 30 min), DNA was blotted overnight via capillary transfer to Nytran (Schleicher & Schuell) in 20×SSC buffer. The blot was washed, UV cross-linked, and prehybridized with Church buffer at 65° C. A 390 bp $^{32}$P-labeled homologous probe (prepared by random primer labeling) was hybridized overnight at 65° C. and the blot was visualized in a Molecular Dynamics model 400S phosphorimager (Molecular Dynamics). The 390 bp probe hybridized to a 6.7 kb wild type DNA fragment and an 8.9 kb knockout DNA fragment. The results of the Southern blot are shown in FIG. 4.

Figure 4:
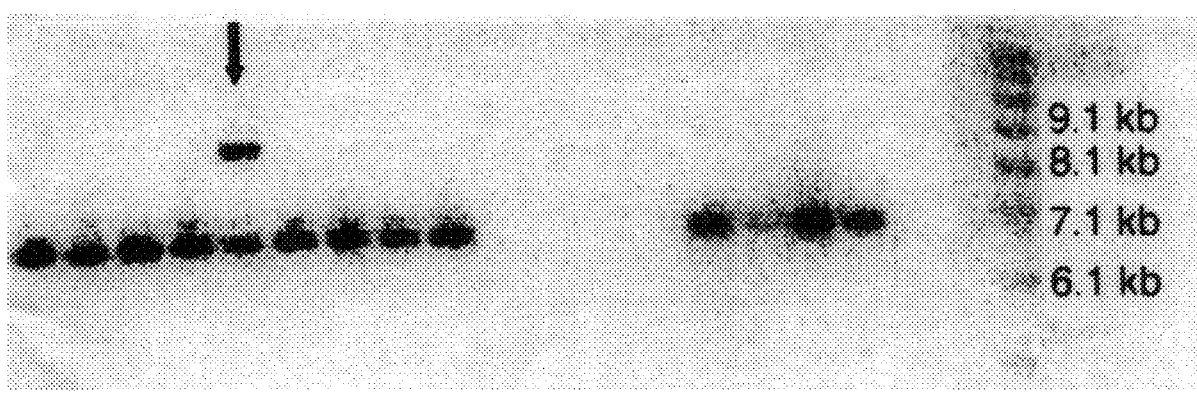
FIG. 4 shows a radiograph of a Southern blot of embryonic stem cells transfected with the pγ3 targeting vector.

FIG. 4 is a Southern blot of D3 agouti ES cells transfected with a disrupted agouti 129 γ3 gene. The endogenous γ3 locus was represented by a 6.7 kb HindIII fragment, while the targeted locus was represented by a 8.9 kb HindIII fragment (FIG. 4).

A low targeting efficiency of greater than 1:150 was obtained following electroporation of the first targeting vector (which contained a disrupted BALB/c γ3 gene) into agouti D3 [Doetschman et al. (1985) J. Embryol. Expt. Morphol. 87:27–45] and R1 [Nagy et al. (1993) Proc. Natl. Acad. Sci. USA 90:8424–8428] embryonic stem cells, respectively. Higher targeting efficiencies (i.e., approximately 1:30) were obtained by introducing the second targeting vector (which contained a disrupted agouti 129 mouse γ3 gene) into the agouti D3 [Doetschman et al. (1985) supra] and R1 [Nagy et al. (1993) supra] embryonic stem cell lines, and into the E 14.1 embryonic stem cell line [M. L. Hooper, (1989) In "Vectors as Tools for the Study of Normal and Abnormal Growth and Differentiation," Lother H. et al. (Eds.), Springer Verlag, Berlin, N.Y., pp. 9–15; Hooper et al. (1987) Nature 326:292–295] from the 129/Ola mouse strain (Harlan Srague Dawley; Harlan Olac, Ltd.). The D3, R1 and the E 14.1 which contained the disrupted agouti 129 mouse γ3 gene were used for the generation of transgenic mice.

c) Generation and Genotyping of Transgenic Mice

Figure 5:
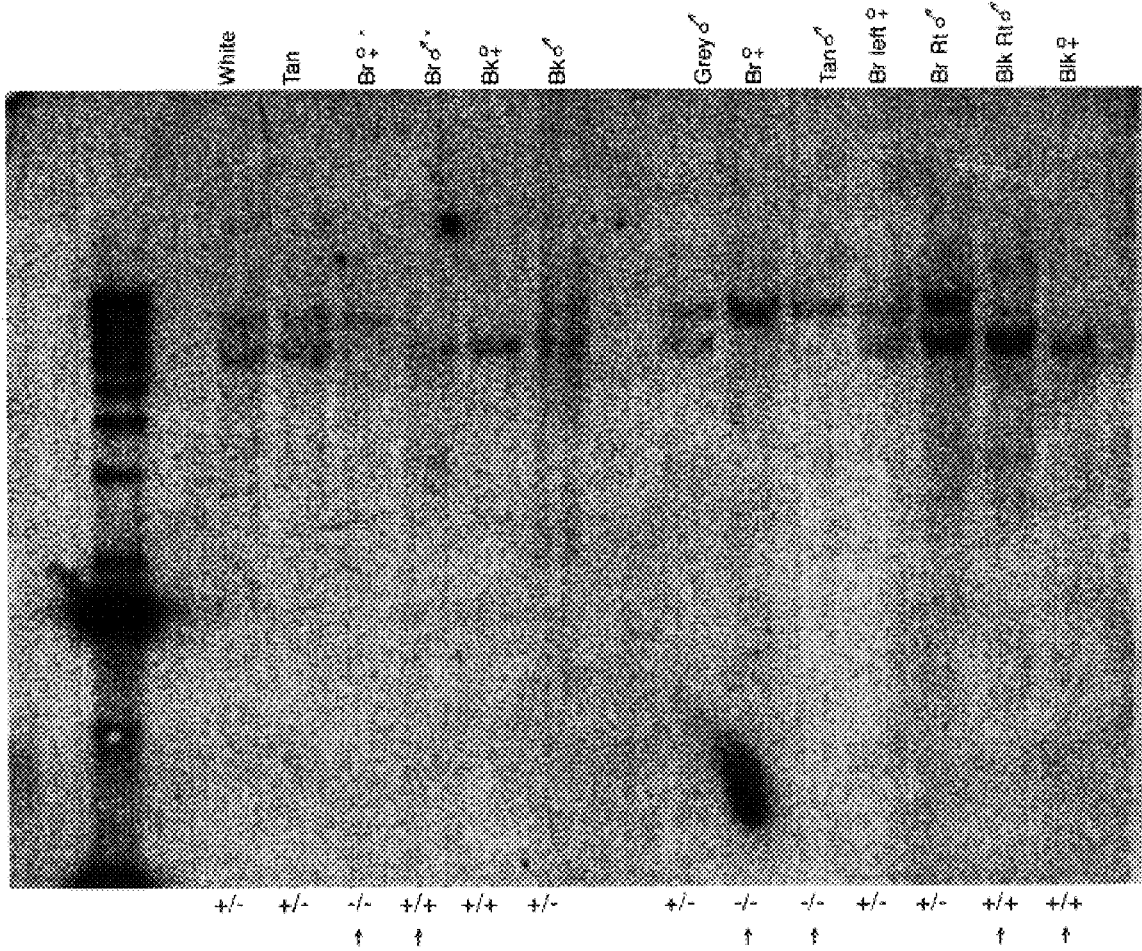
FIG. 5 shows a radiograph of a Southern blot of genomic DNA from animals generated by mating founder mice derived from embryonic stem cells transfected with the pγ3 targeting vector. DNA was derived from wild type (+/+) mice and transgenic mice which were heterozygous (+/−) and homozygous (−/−) for the deletion in γ3.

Once identified by Southern blotting, targeted embryonic stem cell lines were karyotyped and prepared for freezing. The targeted cell lines with the most normal chromosomal profiles determined microscopically were then used for injection into blastocysts in order to produce founder chimeric animals. Southern blot analysis of genomic mouse tail DNA clippings digested overnight with HindIII was performed as described above with the same 390 bp probe. Both the 6.7 kb and 8.9 kb fragments were obtained from heterozygous mice, while homozygous knockouts had only an 8.9 kb DNA fragment (FIG. 5).

Although a good targeting frequency of approximately 1:30 was achieved using the D3 and R1 agouti embryonic stem cell lines, germline transmission from chimeric mice was not achieved when embryonic stem cells were introduced into CD1 blastocysts and the manipulated blastocysts implanted into pseudopregnant CD1 females (Charles River, Michigan). Thus, the E 14.1 embryonic stem cell line from the 129/Ola mouse strain was subsequently used since it has previously been shown to yield a high likelihood of germline transmission. The γ3 targeted 14.1 embryonic stem cells were injected into C57BL/6 blastocysts which were then transferred to the uterus of pseudopregnant F1 CH3B16 females. Male coat color chimeric mice were then bred to NIH Swiss Black females (Tac:N:HIHS-BC) (Taconic). Successful chimeric germline contribution from the targeted embryonic stem cell line was then seen in resultant agouti color pups (in contrast to black pups without germline contribution). The presence of the γ3 mutation (FIG. 5) demonstrates germline transmission of the γ3 mutation to the progeny and the generation of homozygous γ3 −/− transgenic mice.

d) Absence of IgG3 Expression in Transgenic Mice

In order to determine whether the γ3 mutation resulted in abrogation of expressed IgG3, circulating blood levels of IgG3 in wild type (γ+/+), heterozygous γ (+/−), and homozygous (γ−/−) animals were determined using ELISA and Western blotting. Membrane bound IgG3 levels are determined using Fluorescence Activated Cell Sorting (FACS).

i. ELISA

Total serum IgG3 levels were determined using an ELISA assay as follows. Corning 96 well ELISA plates (Corning, Catalogue No. 25802) were coated overnight at 4° C. with 0.1 μg/well (100 μl, 1.0 μg/ml) anti-murine Ig (Southern Biotechnology, Kit No. 5300-04) in phosphate buffered saline (PBS, 60 mM NaPhosphate, 150 mM NaCl, pH 7.2) and blocked with blocking buffer (1% BSA (Sigma Fraction V, Catalogue No. A9306) in PBS) for 1 hour at room temperature. Blocked wells were incubated overnight at 4° C. with serial dilutions (1:1800, 1:5400, 1:16200, 1:48600, 1:145800, 1:437400, 1:1312200 in blocking buffer) of sera from naive (unimmunized) wild type (+/+) and knockout (−/−) mice (all dilutions were added to duplicate wells of the plate). Bound immunoglobulins were detected by the addition of 100 μl per well of a 1:1000 dilution of IgG3-specific alkaline phosphatase (AP) conjugated secondary antibodies (Southern Biotechnology, Kit No. 5300-04) in blocking buffer and incubation for one hour at room temperature, followed by development with 100 μl per well pNPP chromogenic substrate solution [p-Nitrophenyl Phosphate, disodium, 5 mg/tablet per 10 ml DEA buffer (0.5 mM magnesium chloride, 0.02% sodium azide, 10% diethanolamine, pH 9.8)] following the manufacturer's instructions (Sigma, Procedure No. 104). Absorbance was determined at 410 nm in a Dynatech MR5000 UV Spectrophotometer. Control, purified murine IgG3 (Southern Biotechnology, Catalogue No. 5300-01) and sera from heterozygous (+/−) mice were diluted and analyzed according to the same protocol used for knockout and wild-type sera.

Figure 6:
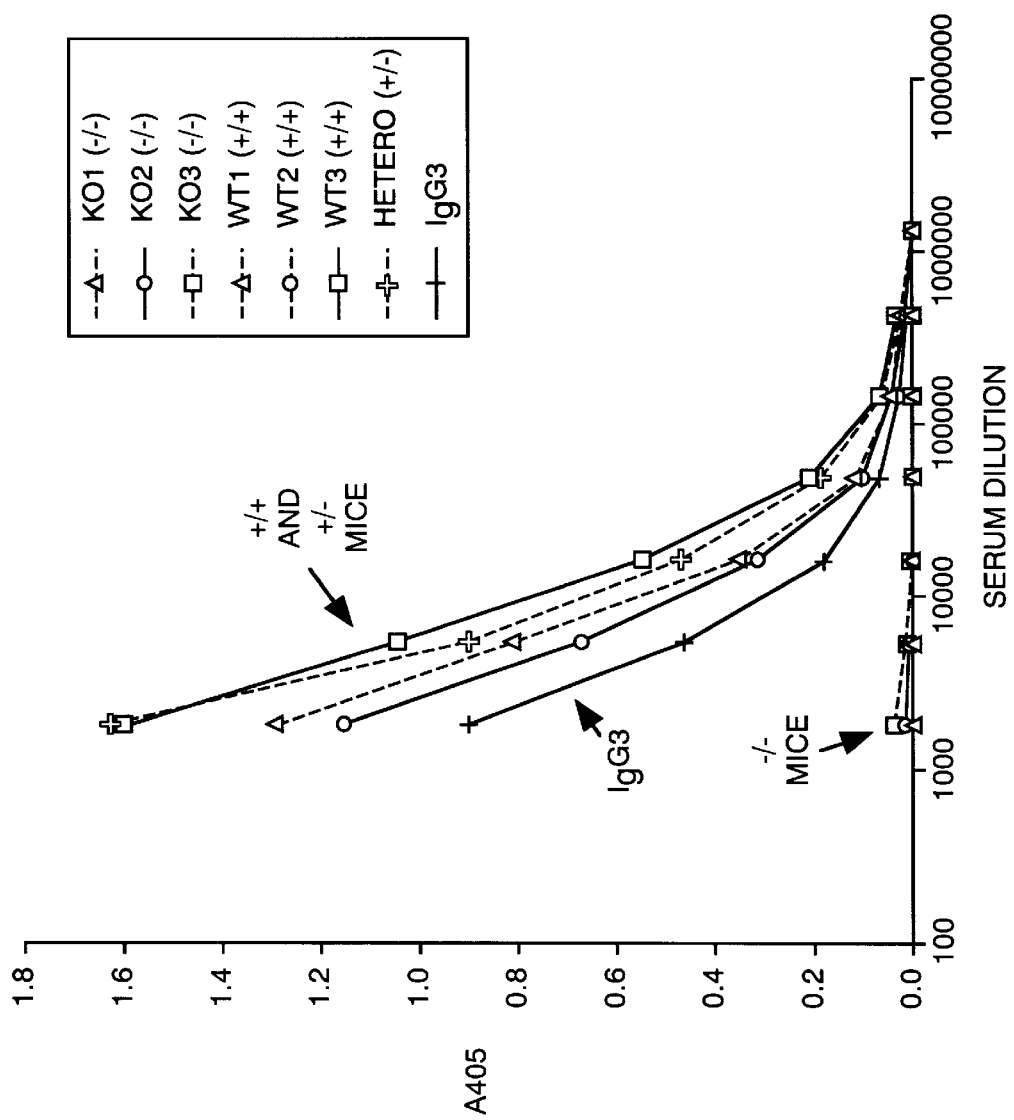
FIG. 6 shows serum IgG3 levels determined by ELISA in wild-type (WT) and transgenic homozygous IgG3-KO (KO) mice.

The results of the ELISA analysis for three wild type (WT1, WT2 and WT3), one heterozygous (Hetero), three homozygous (KO1, KO2, and KO3) animals, and control mouse IgG3 (IgG3) (Southern Biotech.) are shown in FIG. 6. FIG. 6 shows that whereas the levels of IgG3 in the heterozygous transgenic mice were within the same range as the levels in wild type mice, IgG3 levels were undetectable in mice which were homozygous for the γ3 mutation. These data demonstrate that the deletion in the γ3 gene was successful in reducing serum IgG3 to undetectable levels. The complete depletion of serum IgG3 levels in the IgG3-KO mice of this invention is in contrast to the significant levels of serum IgG3 levels detected in the XID mouse [I. Scher (1982) Adv. Immunol. 33:1; Thomas et al. (1993) Science 261:355–358].

ii. Western Blots

Western blot analysis was performed in order to confirm the absence of circulating IgG3 in homozygous γ−/− transgenics. 12 μg serum protein (as determined by a modified Lowry assay, Peterson (1983) Methods in Enzymology 91:95–119) from wild type (WT) or homozygous knockout (KO) mice were loaded into each well (4 μl per well) of a reducing 12% polyacrylamide separating gel with a 4% stacking gel (Biorad). Proteins were separated electrophoretically at a constant 200 volts for approx. 45 minutes (until the dye front had reached the bottom of the gel) and transferred by electroblot (Biorad, 80 V for 60 minutes) to nitrocellulose. The blot was blocked overnight submerged in 1% BSA/PBS (blocking buffer as described supra for the ELISA protocol). Blots were stained one hour with a γ3 H-chain specific AP conjugate (Southern Biotechnology, Catalogue No. 5300-04) diluted 1:1000 in 1% BSA/PBS, 15 ml per blot. Blots were washed extensively with PBS and were visualized by the addition of NBT (Biorad, Catalogue No. 170-6532)/BCIP (Biorad Catalogue No. 170-6539) chromogenic substrate solution according to the manufacturer's protocol (Biorad, Document No. 9139). Control wells contained IgG1 (0.25 μg) or IgG3 (0.25 μg) (both from Southern Biotechnology, Kit No. 5300-01), or broad range molecular weight standards (Southern Biotechnology, Catalogue No. 72807A). IgG1 was used as an internal control to confirm the specificity of the anti-IgG3 antibody used to develop the blots.

Figure 7:
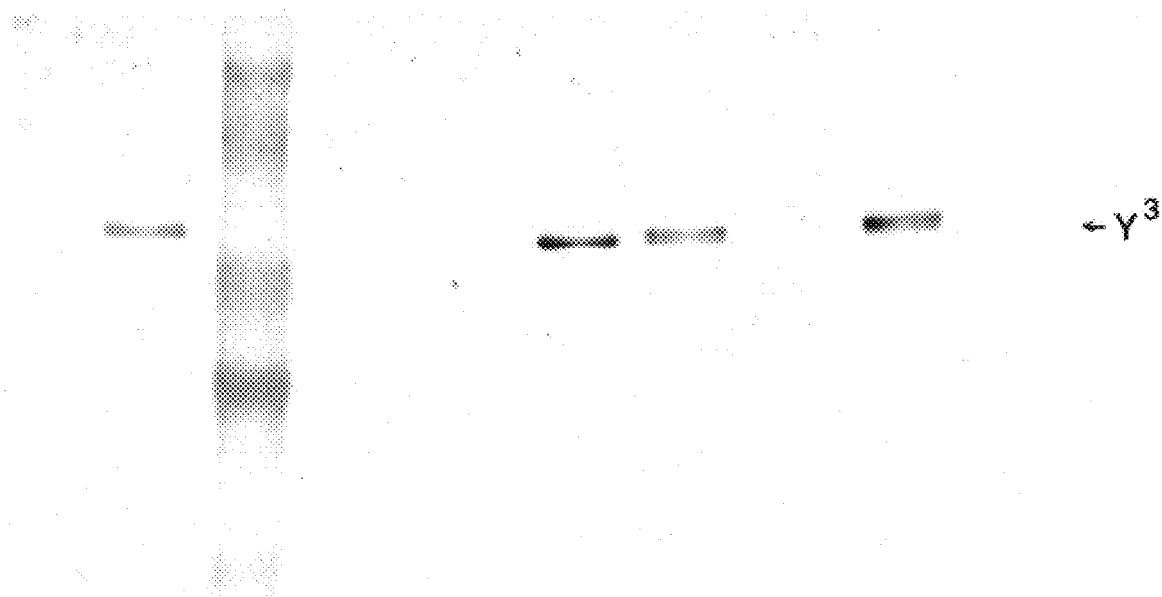
FIG. 7 shows a Western blot of serum IgG3 from wild-type (WT) and transgenic homozygous IgG3-KO (KO) mice.
Figure 9C:
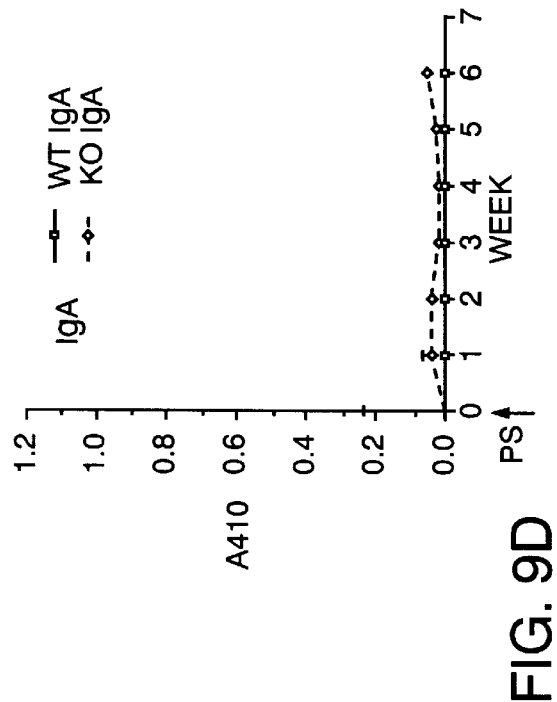
FIG. 9 shows the antibody response of wild-type (WT) and transgenic homozygous IgG3-KO (KO) mice as measured by ELISA following treatment with *Pseudomonas aeruginosa* high molecular weight polysaccharides.
Figure 9D:
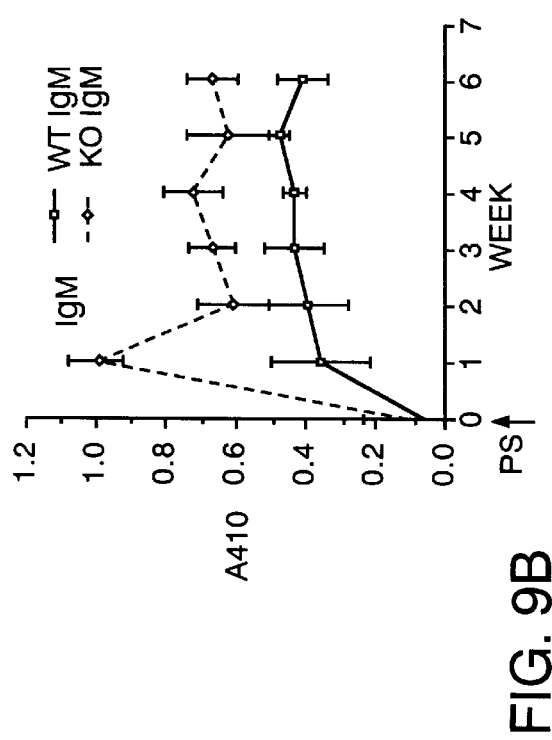
Figure 9A:
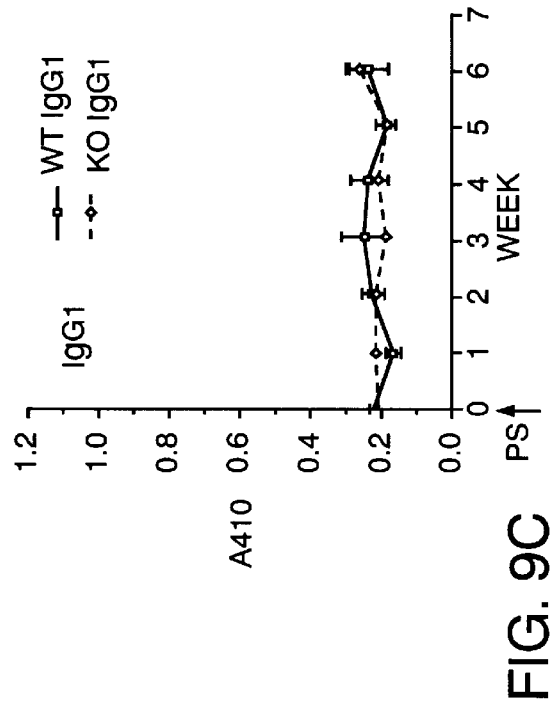
Figure 9B:
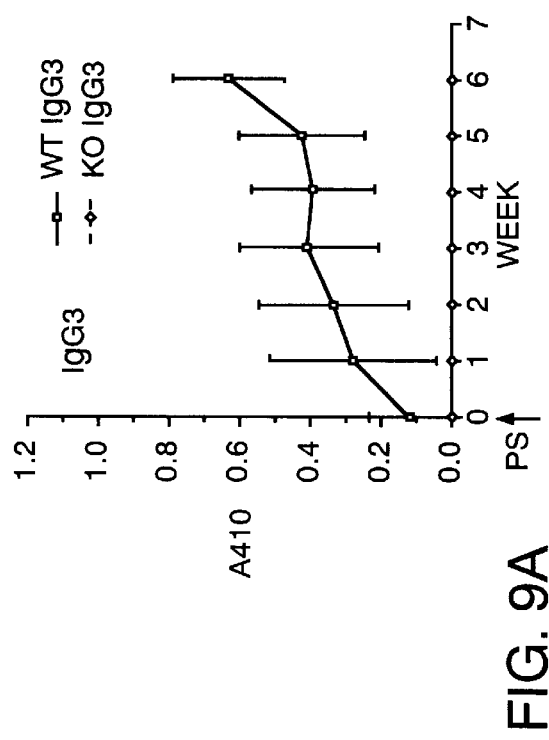
Figure 9F:
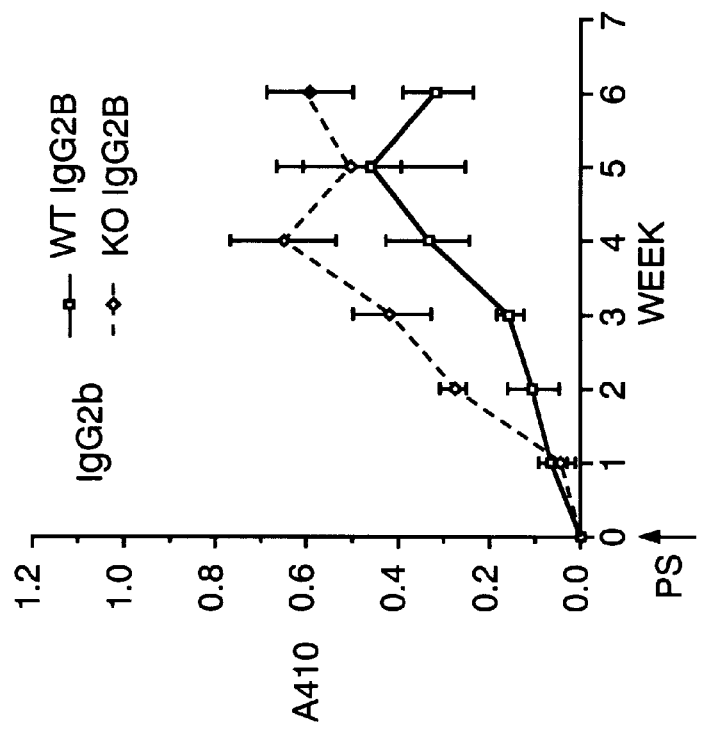
Figure 9E:
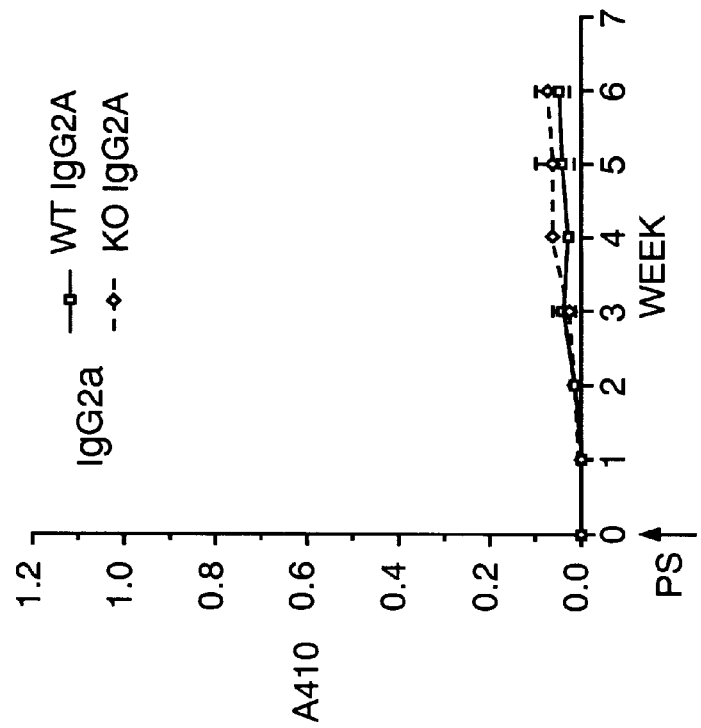

The results of the Western blot analysis for three homozygous (KO1, KO2, and KO3) and three wild type (WT1, WT2, and WT3) mice are shown in FIG. 7. The absence of IgG3 in protein samples derived from the homozygous mice confirmed the absence of detectable circulating IgG3 in homozygous transgenic mice. These data further demonstrate the total abrogation of IgG3 expression as a result of the γ3 mutation.

iii. FACS

To determine the level of membrane bound immunoglobulins in IgG3-KO transgenic mice, an assay for splenic and/or peripheral B cell membrane bound immunoglobulins was standardized using B-cell surface markers by treating animals with a B-cell mitogen, labelling cell surface B-cell antibodies and separating the labelled B-cells from T-cells. This was done as follows. Spleens were removed from euthanized BALB/c which had been immunized with saline or a mitogenic oligonucleotide (CpG) (Operon, Alameda, Calif.). Spleen cell suspensions were prepared using standard procedures. Red blood cells were removed by incubation of the cells in cold ammonium chloride lysing buffer (155 mM NH$_4$Cl, 17 mM Trizma, pH 7.2). Splenic cells were double stained with PE-labeled anti-B220 (Pharmingen, San Diego, Calif.) (a B-cell marker) followed by staining with FITC-labeled anti-MHC class II antibody (anti-I-A$^d$; Pharmingen, San Diego, Calif.). Unlabeled anti-FcγR antibody was also added to prevent non-specific binding of antibody via the Fc receptor. After washing with staining buffer, the cells were resuspended and fixed with paraformaldehyde. Cells (10,000 cells per sample) were then analyzed in a Becton-Dickinson Flow Cytometer (FACS scan, San Jose, Calif.). The histograms of the FACS-separated cells are shown in FIG. 8. Histograms were obtained for cells from control animals treated with saline (FIG. 8A) or CpG oligonucleotide mitogen (FIGS. 8B and 8C). B-cells (right hand side of histogram) were readily separated from T-cells (left hand side of histogram) using the anti-MHC FITC-labeled antibody (FIG. 8A), and increased numbers and/or fluorescence of the B-cells could be detected after mouse exposure to the B-cell mitogen (FIG. 8B). In addition, surface IgM of B-cells could be detected with a FITC-labeled anti-μ antibody (FIG. 8C). These data show that B-cell surface immunoglubulins can be detected using the above described approach.

The levels of surface subclasses of IgG (e.g., IgG1, IgG2a, IgG2b and IgG3) in control (i.e., saline treated) IgG3-KO mice and in IgG3-KO mice treated with fluorescein conjugated anti-mouse immunoglobulin antibodies (Pharmingen, San Diego, Calif.) are measured using the above described protocol. The levels of membrane-bound immunoglobulin isotypes are measured in order to determine whether the disrupted γ3 gene alters the constitutive expression of immunoglobulin isotypes of the γ3 gene.

EXAMPLE 2

Breeding γ3 −/+ Transgenic Mice to Obtain γ3 −/− Transgenic Mice In Different Genetic Backgrounds Transgenic mice which are homozygous for the γ3 mutation and which have different genetic backgrounds are generated as follows. In order to confirm that the resulting progeny are homozygous for the γ3 mutation, DNA from tail biopsies is digested with HindIII for Southern blotting with the 390 bp probe (HindIII/SpeI) described supra (FIG. 3).

DNA from γ3 –/– mice contains an 8.9 kb fragment in the absence of a 6.7 kb fragment.

A) Homozygous 129Ola/Swiss Black Transgenic Mice

In order to create animals that are homozygous (i.e., γ3 –/–) for the γ3 mutation, mixed 129 Ola/Swiss black mice which are heterozygous for the targeted allele (i.e., γ3 +/–) and which are generated as described in Example 1 by interbreeding of chimeric male mice with Swiss Black females are interbred using standard procedures (Bradley, [1987], in *Teratocarcinomas and Embryonic Stem Cells: A Practical Approach*" E. J. Robertson (ed), Oxford: IRL Press, pp. 113–151; and Capecchi, [1989] Science 244:1288–1292.

B) Homozygous Inbred BALB/c Transgenic Mice

Since much of the data in mice concerning immunity to PS antigens has been obtained using BALB/c mice, and since inbred mice have less phenotypic variation in response to immunogens and/or infections, inbred BALB/c transgenic mice which are homozygous for the γ3 mutation are produced. The γ3 –/– transgenic mice with a mixed 129 Ola/Swiss black genetic background (described above) are bred with BALB/c mice to generate heterozygous offspring. The heterozygotic offspring are backcrossed with BALB/c mice for approximately 10 generations in order to obtain a γ3 –/– inbred BALB/c colony.

An alternative method which avoids the time consuming and expensive practice of backcrossing mice for 10 generations is used to generate γ3 –/– transgenic mice in a BALB/c background. Chimeric males generated as described in Example 1 are mated with BALB/c mice to generate heterozygous offspring. The heterozygous offspring are then bred with BALB/c mice and the genome of the resulting offspring is tested for simple sequence length polymorphism (SSLP) markers of the 129 strain and the BALB/c strain using tail DNA and PCR. Briefly, crude DNA samples are prepared from tail samples and approximately 100 ng of each sample is tested in a 20 μl hot start PCR reaction with 40 cycles at 95° C., 30 sec.; 60° C., 30 sec. after which 10 μl of each PCR reaction is electrophoresed on 15 cm vertical 8% non-denaturing polyacrylamide gels, stained with ethidium bromide, and photographed. A 25 bp ladder (BRL, Gaithersburg, Md.) is used as a size standard and allele sizes are estimated based on the known allele sizes in various inbred strains [Dietrich et al. (1996) Nature 380:149–152; Dietrich et al. (1994) Nature Genetics 7:220–245]. SSLP markers which differ between an inbred 129 strain and BALB/c strain are screened using methods known in the art. Mice which contain more BALB/c strain SSLP markers than 129 strain markers are further bred, in order to accelerate the production of an inbred BALB/c strain in as few as three generations.

C) Homozygous Inbred MRL/MpJ-lpr/lpr Transgenic Mice

In order to generate transgenic homozygous γ–/– mice which are congenic on an inbred MRL/MpJ-lpr/lpr background, the γ3 –/– transgenic mice with a mixed 129 Ola/Swiss black genetic background (described above) are bred with MRL/MpJ-lpr/lpr mice (Jackson) to generate heterozygous offspring. The heterozygotic offspring are backcrossed with MRLlMpJ-lpr/lpr mice for approximately 10 generations in order to obtain a γ3 –/– inbred MRL/MpJ-lpr/lpr colony.

Alternatively, a transgenic homozygous γ–/– mouse strain which is congenic on an inbred MRL/MpJ-lpr/lpr background may be produced in as few as three generations by using SSLP markers, described supra. The chimeric males of Example 1 are mated with MRL/MpJ-lpr/lpr mice to generate heterozygous offspring, which are then bred with MRL/MpJ-lpr/lpr mice. The genome of the resulting offspring is tested for simple sequence length polymorphism (SSLP) markers of the 129 strain and the MRL/MpJ-lpr/lpr strain using tail DNA and PCR as described supra. SSLP markers which differ between an inbred 129 strain and MRL/MpJ-lpr/lpr strain are screened using methods known in the art, and mice which contain more MRL/MpJ-lpr/lpr strain SSLP markers than 129 strain markers are further bred, in order to accelerate the production of an inbred MRL/MpJ-lpr/lpr strain containing the γ –/– mutation.

EXAMPLE 3

Immunoglobulin Response of γ3 –/– Mice Having 129 Ola/Swiss Black Background To Cell wall Polysaccharide Antigens In order to determine whether the homozygous γ–/– transgenic mice of this invention are useful as a model for screening different candidate vaccines against infection with polysaccharide-coated bacteria, the antibody response to cell wall polysaccharides was measured in control wild type and in first generation transgenic γ3 –/– 129 Ola/Swiss Black mice produced from founder chimerics. This Example involved (A) immunization with polysaccharide antigens, and (B) detection of antibody response.

A) Immunization With Polysaccharide Antigens

Wild type and γ3 –/– mice were immunized with cell wall polysaccharide, also referred to as high molecular weight polysaccharide (high MW PS), prepared according to the method of Pier [G. B. Pier (1995) J. Infect. Dis. 151:575; Pier et al. (1978) Infect. Immun. 22:908]. Administration was performed essentially as described by Schreiber et al. [Schreiber et al. (1991) J. Immun. 146:188–193]. Briefly, a single 10μg dose of high MW PS was administered intraperitoneally (i.p.) in the absence of adjuvants and the mice were bled weekly for antibody titer.

B) Detection of Antibody Response

The isotype and subclass-specific polysaccharide antibody response in mice treated with the antigens described supra was measured using ELISA to determine soluble immunoglobulin levels and FACS analysis to determine the levels of membrane bound inmnunoglobulins.

For ELISA assay, high molecular weight polysaccharide derived from the O-side chain of type 1 Pseudomonas aeruginosa lipopolysaccharide (LPS) prepared as previously described [G. B. Pier (1982) J. Clin. Invest. 69:303–308; Pier et al. (1978) Infect. Immun. 22:908–918] (4 μg/ml, 100 μl per well), was coated onto ELISA plates (Coming, Catalogue No. 25802) in PBS overnight at 4° C. Unbound sites were blocked with 240 μl per well of a 1% BSA/PBS solution (blocking buffer, see Example 1, supra) for 1 hour at room temperature. Serial three-fold dilutions beginning with a dilution of 1:200 of sera from weekly bleeds obtained from mice immunized intraperitoneally with 10 μg (100 μg/ml in PBS) of the same polysaccharide were incubated in duplicate wells, 100 μl/well in blocking buffer overnight at 4° C. Bound antibody was detected with sub-isotype specific AP-conjugated secondary reagents followed by the addition of pNPP chromogenic substrate as for the total serum IgG3 ELISA described supra, except that substrate development times were substantially longer (i.e., between 120 or 180 minutes, depending on the isotype). The results of the ELISA analysis are shown in FIG. 9.

FIG. 9 shows the antibody response in wild type and γ3 –/– mice treated with cell wall polysaccharides. FIG. 9 shows that the transgenic mice were capable of mounting an IgM and IgG2b response in the absence of an anti-polysaccharide IgG3 response. This demonstrates that the γ3 mutation did not disrupt genes which are located upstream (i.e., the μ gene) or downstream (ie., γ2b gene) of the γ3 gene. In other words, the transgenic mice of the present invention retained their ability for immunoglobulin switching as demonstrated by the expression of an IgG2b anti-polysaccharide response. Furthermore, the levels of IgG2b induced in response to polysaccharide challenge in the transgenic mice were higher than those induced in wild type mice. This data shows that the transgenic animals are capable of compensating for their deficient IgG3 expression by producing higher levels of other IgG subtypes.

For FACS analysis, spleens from naive IgG3-KO mice or IgG3-KO mice immunized with type 1 *Pseudomonas aeruginosa* high molecular weight polysaccharides were removed into phosphate buffered saline (PBS). Single cell suspension were prepared by grating the splees over a wire mesh. Red blood cells were removed by incubation with an ammonium chloride lysis buffer. Tubes containing $10^6$ cells were incubated first with a non-specific anti-Fc$\gamma$ block, then with fluorescently-labeled antibodies (or fluorescently-labeled isotype-matched controls. All cells were stained with PE-anti-B220 as described above. Fluorescence in the second channel (FITC label) monitored the presence of surface immunoglobulin isotypes and T cell markers. FACS analyses (10,000 cells per sample) were performed on a Becton Dickenson FACScan using Lysis II analysis software.

EXAMPLE 4

Effect of Immunization of Trangenic Mice With Polysaccharide Antigens or With Anti-Polysaccharide Antibodies On Bacterial Infection In order to use the transgenic mice of the present invention as a model for screening candidate polysaccharide antigens and anti-polysaccharide antibodies (described in Example 3) for their efficacy in protecting IgG2-deficient humans against infection with polysaccharide-coated bacteria, transgenic homozygous ($\gamma$3 $-/-$), heterozygous ($\gamma$3 $+/-$) and control wild-type ($\gamma$3 $+/+$) mice are treated with the candidate compositions and the response of the treated mice to local and systemic bacterial infections is determined. This Example involves (A) preparation of anti-cell wall polysaccharide monoclonal antibodies, (B) ELISA for detection of anti-idiotypic and cell wall polysaccharide antibodies, and (C) mouse protection model.

A. Preparation of Anti-Cell Wall Polysaccharide Monoclonal Antibodies

Production of monoclonal antibody (mAbl) directed to cell wall polysaccharide (also referred to as high molecular weight polysaccharide) has been previously described in detail [Schreiber et al, (1990) J. Immunol. 14:1023; Powderly et al. (1988) J. Immunol. 140:2746]. Briefly, 8-week-old BALB/c ByJ mice were hyperimmunized with high molecular weight polysaccharides and their spleen cells fused with the P3U1 mouse myeloma cell line. Hybridomas were screened for anti-high molecular weight antibody in the ELISA described below. Positive hybrids were cloned by limiting dilution, and a clone that produces anti-high polysaccharide antibody of the IgG3 isotype was chosen for further experiments.

Anti-idiotypic monoclonal antibodies (mAb2) were produced by immunizing 8-week-old BALB/c ByJ mice with 10 $\mu$g mAb1 and CFA twice per week for 5 weeks, and performing fusion experiments with the SP2/0 mouse myeloma cell line as previously described [Schreiber et al. (1990) supra]. The presence of anti-Id was determined using an F(ab')2 ELISA described below, and positive hybridomas were cloned repeatedly by limiting dilution. A clone that produces an anti-Id of the IgG1 isotype was used for further experiments.

Anti-Id-induced high molecular weight polysaccharide specific antibodies (Ab3) were elicited in syngeneic mice via immunizations with 10 $\mu$g of monoclonal anti-Id i.p. one per week for 4 weeks without adjuvants. Sera were obtained by tail vein puncture weekly and screened for binding to high molecular weight polysaccharides in ELISA as described below.

B. ELISA for Detection of Anti-Idiotypic And Cell wall Polysaccharide Antibodies Sera or supernatants from clones were screened for anti-Id (mAb2) in an ELISA using microtiter plates coated with F(ab')2 fragments from anti-high molecular weight polysaccharides monoclonal antibody (mAb1) as previously described [Schreiber et al. (1990) supra]. Each F(ab')2 preparation was screened for purity using SDS-PAGE or using ELISA with goat anti-mouse Fc-specific conjugates. Plates were coated with 2.5 $\mu$g/ml of F(ab')2, and then blocked with 1% BSA in PBS for 60 min. After multiple washes, sera or supernatants were added, followed by goat anti-mouse IgG Fc fragment or anti-mouse IgM $\mu$-chain-specific AP conjugates (Cappel Antibodies, Westchester, Pa.). The ELISA was developed using phosphatase substrate (Sigma) and standard procedure as previously described [Schreiber et al. (1990) supra], and read at 410 nm with a Titertek Multiscan ELISA plate reader (Flow Laboratories, McLean, Va.).

Sera or clone supernatants were screened for Ag or anti-id-induced antibodies (Ab1 or Ab3) directed to high molecular weight polysaccharides by coating ELISA plates with 5 $\mu$g/ml tyraminated high molecular weight polysaccharides as described previously [Schreiber et al. (1990) supra]. The high molecular weight polysaccharides were tyraminated via cyanogen bromide coupling when used in ELISA to enhance binding of the Ps to the plastic microtiter ELISA plates. After blocking, sera or supernatants were added and IgG1, IgG2a, IgG2b, IgG3, or IgM anti-Ps antibodies were detected using goat anti-mouse isotype-specific AP conjugates (Southern Biotech, Birmingham, Ala.) in dilutions that yield equal OD with control myeloma proteins. Plates were developed and read as described above. ELISA titers were determined by plotting absorbance versus dilution on semilog graph paper, and end point titers (reciprocal dilutions) were determined by extrapolating the linear portion of the titration curve to a fixed absorbance value of 0.1.

C. Mouse Protection Model

The protective efficacy of anti-Id-induced Ab3 is determined in a neutropenic mouse model of *P. aeruginosa* sepsis. The 6-week-old transgenic mice are given 4 mg of cyclophosphamide i.p. on days 0 and 2. On day 4, 2.0 mg of cyclophosphamide is given, and neutropenia (<$10^3$ PMN/ $mm^3$) confirmed by counting PMN from tail vein blood in a modified Neubauer counting chamber. Two hours after the last dose of cyctophosphamide, 0.15 ml of pooled anti-Id-induced sera, naive mouse sera, or 2.0 $\mu$g of anti-high molecular weight polysaccharides monoclonal antibodies is administered i.p., followed in 2 more hours by $1 \times 10^3$ cfu of washed Id-1 *P. aeruginosa*. The endpoint measured is mortality, and the experiments are terminated 5 days after administration of bacteria.

To determine if the high molecular weight polysaccharide-specific antibodies induced in response to immunization with anti-Id are protective, mice which had seroconverted are bled, the sera pooled, and administered to neutropenic mice which are then challenged with $1 \times 10^3$ It-1 *P. aeruginosa*. Mortality is compared in transgenic IgG3-KO mice receiving pooled sera from high molecular weight polysaccharide seronegative mice (ie., immunized with saline or a nonsense murine monoclonal antibody of the same isotype and quantity as the anti-id) and transgenic IgG3-KO mice receiving either anti-Id-induced antisera containing high molecular weight polysaccharide antibodies, or anti-high molecular weight polysaccharide monoclonal antibodies. In addition to mortality as an endpoint, sepsis, meningitis, and $LD_{50}$ for pneumococcus bacteremia are also measured in transgenic mice challenged with live bacteria. An increase in $LD_{50}$, or a reduction in the percentage of animals suffering from sepsis, death or meningitis following administration of the candidate immunogen demonstrates that the candidate immunogen is effective in preventing and treating bacterial infection.

EXAMPLE 5

Determination of The Role of Elevated IgG3 Levels in The Expression of Systemic Lupus Erythematosus (SLE) Symptoms In MRL/MpJ-lpr/lpr Mice To determine the role of elevated IgG3 levels which are observed in MRLIMpJ-lpr/lpr mice on the expression of SLE-associated glomerulonephritis in these mice, the levels of serum and B cell membrane bound IgG3 as well as other classes and IgG subclasses in wild-type (γ3 +/+) MRL/MpJ-lpr/lpr mice (produced as described in Example 2) are compared to those in transgenic homozygous (γ3 −/−) and transgenic heterozygous (γ3 +/−) MRL/MpJ-lpr/lpr mice using ELISA, Western and FACS analyses as described in Example 1. IgG3 levels are correlated with pathological parameters which are symptomatic of SLE-associated renal disease (e.g., elevated titer of immune complexes, diffuse glomerulonephritis, etc.) in these mice. An association between the absence of IgG3 levels and a reduction or absence of glomerulonephritis pathology in homozygous γ3 −/− transgenic mice suggests that a reduction in IgG3 levels is therapeutic.

As clear from the data presented herein, the present invention solves the problems encountered in the prior art. The present invention provides transgenic animals in which an immunoglobulin subtypes is selectively inactivated in the absence of inactivation of other immunoglobulin isotypes and subtypes. The transgenic animals of the present invention provide a useful model for screening compounds for their relative efficacy in preventing and treating disorders of the immune system in which one or more antibody isotypes or subtypes is involved. The transgenic animals of the present invention provided herein provide the advantage that they contain a discrete genetic alteration in a selected immunoglobulin. Inactivation of a selected immunoglobulin in the transgenic animals provided herein does not adversely interfere with the animal's ability to express other active immunoglobulin isotypes and subtypes. These transgenic animals may be interbred with other animals of a different genetic background to determine the role of a selected immunoglobulin isotype or subtype in disease and to rationally design drugs to treat these diseases.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant art are intended to be within the scope of the following claims.

What is claimed is:

1. A transgenic mouse comprising a genome with a homozygous disruption of the immunoglobulin γ3 gene, wherein said mouse expresses a reduced level of IgG3 relative to a corresponding wild-type mouse, and wherein said transgenic mouse further expresses wild-type level of an antibody selected from the group consisting of IgM and IgG2b.

2. The transgenic mouse of claim 1, wherein the genome of said mouse comprises one or more deletions in one or more exons of a γ3 gene.

3. The transgenic mouse of claim 2, wherein said genome further comprises a frameshift mutation within said γ3 gene.

4. The transgenic mouse of claim 2, wherein said genome further comprises a heterologous selectable marker gene.

5. A method for screening a test compound for immunizing activity, comprising:

a) providing:
  i) first and second transgenic mice comprising a genome with a disrupted immunoglobulin γ3 gene, wherein said first and second transgenic mice express a reduced level of IgG3 relative to a corresponding wild-type animal; and
  ii) a composition comprising said test compound; and
b) administering said test compound to said first transgenic mouse to produce a treated animal; and
c) evaluating an immune response to said test compound.

6. The method of claim 5, wherein said test compound is a cell wall polysaccharide.

7. The method of claim 6, wherein said bacterium is *Pseudomonas aeruginosa*.

8. The method of claim 5, wherein said test compound is a capsular polysaccharide.

9. The method of claim 8, wherein said bacterium is *Streptococcus pneumoniae*.

10. A method for producing a transgenic mouse, wherein said mouse expresses a reduced level of IgG3 relative to a corresponding wild-type mouse, comprising:

a) providing:
  i) an embryonic stem cell comprising wild-type γ3 genes;
  ii) a blastocyst of a mouse;
  iii) a pseudopregnant mouse; and
  iv) an oligonucleotide sequence comprising at least a portion of a non-human γ3 gene, said portion comprising one or more deletions in one or more exons of said γ3 gene;
b) introducing said oligonucleotide sequence into said embryonic stem cell under conditions such that said oligonucleotide sequence is homologously recombined into at least one of said wild-type γ3 genes in the genome of said embryonic stem cell to produce a treated embryonic stem cell;
c) injecting said treated embryonic stem cell into said blastocyst to produce an injected blastocyst;
d) introducing said injected blastocyst into said pseudopregnant mouse; and
e) permitting said pseudopregnant mouse to deliver progeny comprising said homologously recombined oligonucleotide, wherein said progeny express a reduced level of IgG3 relative to a corresponding wild-type mouse.

11. The method of claim 10, wherein said oligonucleotide sequence comprises a deletion of the nucleotide sequence of SEQ ID NO:9.

* * * * *